United States Patent [19]
Carlow et al.

[11] Patent Number: 5,482,850
[45] Date of Patent: Jan. 9, 1996

[54] METHOD FOR IDENTIFYING ANTI-PARASITIC COMPOUNDS

[75] Inventors: Clotilde K. S. Carlow, Cambridge; Antony Page, Beverly, both of Mass.

[73] Assignee: New England Biolabs, Inc., Beverly, Mass.

[21] Appl. No.: 145,995

[22] Filed: Oct. 29, 1993

[51] Int. Cl.$^6$ .................... A61K 38/16; C07K 14/435; C12N 9/90

[52] U.S. Cl. .................... 435/233; 514/12; 530/350

[58] Field of Search .................... 530/350; 514/12; 435/233

[56] References Cited

PUBLICATIONS

Aga et al., J. Pavas, et al. vol. 79(4) 600–664 (1992).
Kieffert et al. J. Biol. Chem. vol. 268(17) pp. 12303–12310 (1993).
Lawrence Para Imm. A D371 (1992) Lee et al. Science 239 p. 1288 (1988).
Fischer, et al., *Nature*, 337:476–478 (1989).
Takahashi, et al., *Nature*, 337:473–475 (1989).
Bachinger, *J. Biol. Chem.*, 262:17144–17148 (1987).
Steinmann, et al., *J. Biol. Chem.*, 266:1299–1303 (1991).
Lui, et al., *Biochemistry*, 30:2306–2310 (1991).
Schreiber & Crabtree, *Immunol. Today*, 13:136–142 (1992).
Behforouz, et al., *J. Immunol.* 136:3067–3075 (1986).
Nilsson, et al., *Parasitol. Immunol.*, 7:19–27 (1985).
Pons, et al., *Exper. Parasitol.*, 67:190–198 (1988).
Munro & McLaren, *Parasitol.*, 100:19–29 (1990a).
Munro & McLaren, *Parasitol.*, 100:29–34 (1990b).
Hashiguchi & Okamura, *J. Helminthol.*, 62:251–256 (1988).
Wastling, et al., *Parasitol.*, 104:531–538 (1992).
Bout, et al., *Trans. Roy. Soc. Trop. Med. Hyg.*, 78:670–671 (1984).
Zahner & Schulthesis, *J. Helminthol.*, 61:282–290 (1987).
Bolas–Fernandez, et al., *Parasit. Immunol.*, 10:111–116 (1988).
Koletsky, *J. Immunol.*, 137:1054–1059 (1986).
Argaet & Mitchell, *J. Parasitol.*, 78:660–664 (1992).
Lightowlers, et al., *Mol. Biochem. Parasitol.*, 36:287–290 (1989).
Chappell & Wastling, *Parasitol.*, 105:S25–S40 (1992).
Lawrence, et al., *Parasit. Immunol.*, 14:371 (1992).
Anderson, et al., *Proc. Natl. Acad. Sci. USA*, 90:542–546 (1993).
Kieffer et al., *J. Biol. Chem.*, 268:12303–12310 (1993).
Bartling, et al., *Plant Mol. Biol.*, 19:529–530 (1992).
Haendler, et al., *EMBO J.*, 6:947–950 (1987).
Hasel & Sutcliffe, *Nucleic Acids Res.*, 18:4019 (1990).
Gasser, et al., *Proc. Natl. Acad. Sci.*, 87:9519–9523 (1990).
Stammes, et al., *Cell*, 65:219–227 (1991).
Haendler, et al., *Gene*, 83:39–46 (1989).
McCombie, et al., *Nature Genet.*, 1:124–131 (1992).
Ke, et al., *Proc. Natl. Acad. Sci. USA*, 88:9483–9487 (1993).

*Primary Examiner*—Mindy B. Fleisher
*Assistant Examiner*—David Schmickel
*Attorney, Agent, or Firm*—David G. Conlin; Gregory D. Williams; David S. Resnick

[57] ABSTRACT

The present invention relates to the use of these cyclophilins, hereinafter referred to as "cyclophilin-like proteins (CLP)", in a method for identifying compounds capable of binding to and/or inhibiting the enzymatic activity of these proteins. Such compounds may be further screened for their ability to inhibit parasites which are not susceptible to the anti-parasitic effects of CsA.

2 Claims, 11 Drawing Sheets

```
          /EcoRI
  1-GAATTCCGGGCGAAATAATGCTAATTTTCTTATTTAATCCTACTATTGTGACGGAAAA ATGTCAAAAAAGATCGCCGCGG-80
      I  P  A  K  *  C  *  F  S  Y  L  I  L  L  L  *   R  K  M  S  K  K  D  R  R  R

81-GTATTTTGGATGTAACAATTGATGGTAACCCTTGCGGGTCGAATTGTACAATGATATAGCACCACGGAC-160
      V  F  L  D  V  T  I  D  G  N  L  A  G  R  I  V  M  E  L  Y  N  D  I  A  P  R  T

161-GTGTAATAATTTCCTGATGCTTTGTACTGGTATGGCAGGTAAGATTAGTGGCAAACCTTTGCACTACAAAGGAT-240
      C  N  N  F  L  M  L  C  T  G  M  A  G  T  G  K  I  S  G  K  P  L  H  Y  K  G  S

241-CAACATTTCATCGTGTCATCAAAAATTTCATGATTCAGGGAGGTGATTTTACGAAAGGTGGGGAATCA-320
      T  F  H  R  V  I  K  N  F  M  I  Q  G  G  D  F  T  K  G  D  G  T  G  G  E  S

/EcoRI
321-ATTTATGGTGGTATGTTTGACGATGAAGAATTCGTTATGAAACATGATGAACCGTTTGTTGTCGATGGGCAACAAGGG-400
      I  Y  G  G  M  F  D  D  E  E  F  V  M  K  H  D  E  P  F  V  V  S  M  A  N  K  G

401-ACCTAATACGAATGGTTCACAGTTTTTCATTACAACACCTGCGCCACATCTCAATAATATCCATGTGGTATTTGGTA-480
      P  N  T  N  G  S  Q  F  F  I  T  T  P  A  P  H  L  N  N  I  H  V  V  F  G  K

481-AGGTTGTTTCTGGGCAGGAAGTTGTAACCAAAATCGAATATTTAAAAACTAATTCCAAGAATCGTCCACTAGCTGATGTT-560
      V  V  S  G  Q  E  V  V  T  K  I  E  Y  L  K  T  N  S  K  N  R  P  L  A  D  V

561-GTAATACTTAATTGTGGTGAACTTGTTCGACGAAAAAAACGTCAACATTCTTCTAGATCAAATGAATCAGTCAGTTCTTC-640
      V  I  L  N  C  G  E  L  V  R  R  K  K  R  Q  H  S  S  R  S  N  E  S  V  S  S  S

FIG.IA
```

```
641-TACATCAACTGAAAAAGTCACAAAAGACAAAAATGAAAGAAGCGGAAAGAGAGTGATGAAGTGG-720
      T  S  T  E  K  S  H  K  K  T  K  K  M  K  E  K  R  K  E  S  D  E  V  E
721-AACAATTGGAACTGTTGTTCCGGAAGCAGAACTGCAGTTATCGAGCGTAAAAGCTGAAGATTTGCCTGATGAA-800
      Q  L  E  I  G  T  V  V  P  E  A  E  L  Q  L  S  S  V  K  A  E  D  L  P  D  E
801-CCAGATCACCAAAATAAATATCTTATGAGACGATCAAAACGCCAGAAAATTCGAGGAAAGAAAAAGAAAGCAACG-880
      P  D  H  Q  N  K  Y  L  M  R  R  S  K  T  P  E  N  S  R  K  G  K  K  E  K  Q  R
881-ACAATCACCTCATCGCTTTTCGCGACGCGATATTGGTCATCGTTTGAATCGTATGCGGAGAACGGAACCGGACATAAAA-960
      Q  S  P  H  R  F  S  R  R  D  I  G  H  R  L  N  R  M  R  R  T  G  H  K  I
961-TAAAGGGTCGTGGTGCACTTAGATTTCGAACTCCAGAGGGTAGTAGCGACCACGATGGGAGTCGTACTCCTCCCATTGG-1040
      K  G  R  G  A  L  R  F  R  T  P  E  G  S  S  D  H  D  G  S  R  T  P  P  H  W
1041-AGGCGTGAACAGAATCGTGTAATAACACTTGATGAATTGCATCGTTTGCAAGAGAAAAGGAAAGCATATGAGCTTGAAGA-1120
      R  R  E  Q  N  R  V  I  T  L  D  E  L  H  R  L  Q  E  K  R  K  A  Y  E  L  E  E
1121-ACTTGAGAATCCCAAAAAATGATGTCGTCGATAAAGCAAAACTGGTATATATTATTAAACACATCGGAGAAAATTGAAGACA-1200
      L  E  N  P  K  N  D  V  V  D  K  A  K  T  G  I  L  L  N  T  S  E  K  I  E  D  K
1201-AAGAGGAAAGGTATCGCGGTAAGTCTGAAAAGAAGGAAAATCGGCATGAGCGAAGTAGGCACATACAACGCGACGGTCACCG-1280
      E  E  R  Y  R  G  K  S  E  K  K  E  N  R  H  E  R  S  R  H  T  T  R  R  S  P
```

FIG. IB

1281-GAGCATGTAACACGACATTTGTGAAGGAAAAAATCGGCATAAAGTTGATGAGGTTGGGAACAGTGAAGATATGAAACA-1360
      E  H  V  T  R  H  F  V  K  E  K  N  R  H  K  V  D  E  V  G  N  S  E  D  M  K  Q

1361-GACAAAAAGAGATCGACGAGGCGAGCCGATGAAGAAAGTCGAAGTTAATGGTGAAAAAGCTGCTGCAATGGATG-1440
      T  K  R  D  R  R  G  R  A  D  E  K  E  K  V  E  V  N  G  E  K  A  A  M  D  E

1441-AGTTAAATCTGGATGAACCAACAGTAGAGGTTACATTGGACAGTGCCGAAGATATAAGAGATAGTGATGACGAAGCCATT-1520
      L  N  L  D  E  P  T  V  E  V  T  L  D  S  A  E  D  I  R  D  S  D  D  E  A  I

1521-AGGATTCATTTATTGAAAGCAAAAAAATGGCAGAAGAAAACAAGAAAGATGCTTGAAAAGACTGGTGA-1600
      R  I  H  L  L  K  A  K  K  M  A  E  E  K  T  K  Q  E  A  K  M  L  E  K  T  G  D

1601-TAAAGAAGGACGAGATCAAAAGACGATTTCTGAGGCGAAACAGAAGGACAGTGCTGAAAAGATAGGCAGCATCGAGAGC-1680
      K  E  G  R  D  Q  K  T  I  S  E  A  K  Q  K  D  S  A  E  K  D  R  Q  H  R  E  H

1681-ATAAAAATGATGAACTTGAAAAGCGAGCTATTGAGAAACAAGATAAAGATCAAATTGTAGAGAGAGATACAGGGAGTAAA-1760
      K  N  D  E  L  E  K  R  A  I  E  K  Q  D  K  D  Q  I  V  E  R  D  T  G  S  K
                                                                      /EcoRI
1761-CAACGACGAAAAAGTGATAGCAAAGAACACAGAGAGAAGAGAGAGAGAGCCGGAATTC-1823
      Q  R  R  K  S  D  S  K  E  H  R  E  R  E  R  E  P  E  F

FIG. IC

| | | | | | |
|---|---|---|---|---|---|
| 1-MSKKDRRRVF | LDVTIDGNLA | GRIVMELYND | IAPRTCNNFL | MLCTGMAGTG | KISGKPLHYK -Bm |
| 55-MGAQDRPQCH | FDIEINREPV | GRIMFQLFSD | ICPKTCKNFL | CLCSGEKGLG | KTTGKKLCYK -Hnk |
| 1-  MAHCF | FDMTIGGQPA | GRIIMELFPD | .VPKTAENFR | ALCTGEKGIG | P.SGKKMTYE -At |
| 1-  MVNPTVF | FDIAVDGEPL | GRVSFELFAD | KVPKTAENFR | ALSTGEKGFG | ........YK -HA |
| 1-  MVNPTVF | FDITADDEPL | GRVSFELFAD | KVPKTAENFR | ALSTGEKGFG | ........YK -MA |
| 1-  MANPKVF | FDLTIGGAPA | GRVVMELFAD | TTPKTAENFR | ALCTGEKGVG | K.MGKPLHYK -Le |
| 1-  MSTLPRVF | FDMTADNEPL | GRIVMELRSD | VVPKTAENFR | ALCTGEKGFG | ........YK -Dm |
| 12-KQKRNLPRVF | FDIRIGNADR | GRIVMELRSD | IVPRTAENFR | ALCTGDRGFG | ........YH -Sj |
| 1-  GVKCF | FDISIGGKPA | GRIVFALFDD | .VPKTVENFR | ALCTGEKGFG | ........YK -Eg |
| 1-  MSQVY | FDVEADGQPI | GRVVFKLYND | IVPKTAENFR | ALCTGEKGFG | ........YA -Sc |
| ?- | | | | | R -Ce |

FIG. 2A

| | | | | | |
|---|---|---|---|---|---|
| 61 -GSTFHRVIKN | FMIQGGDFTK | GDGTGGESIY | GGMFDDEEFV | MKHDEPFVVS | MANKGPNTNG -Bm |
| 15 -GSTFHRVVKN | FMIQGGDFSE | GNGKGGESIY | GGYFKDENFI | LKHDRAFLLS | MANRGKHTNG -Hnk |
| 54 -GSVFHRVIPK | FMLQGGDFTL | GNGRGGESIY | GAKFADENFI | HKHTTPGLLS | MANAGPGTNG -At |
| 50 -GSCFHRIIPG | FMCQGGDFTR | HNGTGGKSIY | GEKFEDENFI | LKHTGPGILS | MANAGPNTNG -HA |
| 50 -GSSFHRIIPG | FMCQGGDFTR | HNGTGGRSIY | GEKFEDENFI | LKHTGPGILS | MANAGPNTNG -MA |
| 57 -GSTFHRVIPG | FMCQGGDFTA | GNGTGGESIY | GAKFNDENFV | KKHTGPGILS | MANAGPGTNG -Le |
| 51 -GSIFHRVIPN | FMCQGGDFTN | HNGTGGESIY | GNKFPDENFE | LKHTGSGILS | MANAGANTNG -Dm |
| 64 -NCCFHRVIPQ | FMCQGGDFVK | GDGTGGKSIY | GRKFDDENFQ | LRHEGFGVLS | MANSGPNTNG -Sj |
| 47 -GSKFHRIIPG | FMCQGGDFTA | GNGTGGKSIY | GSKFEDENFN | HKHSKPMMLS | MANAGKNTNG -Eg |
| 48 -GSPFHRVIPD | FMLQGGDFTA | GNGTGGKSIY | GGKFPDENFK | KHHDRPGLLS | MANAGPNTNG -Sc |
| ? -DPIFXRIIPN | FMXQGGDFTR | GNGTGGESIY | GEKFPDENFK | EKHTGPGVLS | MANAGPNTNG -Ce |

FIG. 2B

```
121-SQFFITTTPA PHINNIHVVF GKVVSGQEVV TKIEYLKTNS KNRPLADVVI LNCGEL.  -Bm
175-SQFFITTKPA PHLDGVHVVF GLVISGFEVI EQIENLKTDA ASRPYADVRV IDCGVL.  -Hnk
114-SQFFITTVAT PHLDGKHVVF GKVVEGMDVV RKIEATQTDR GDKPLSEVKI AKCGQL*  -At
110-SQFFICTAKT EWLDGKHVVF GKVKEGMNIV EAMERFGSRN G.KTSKKITI ADCGQLE* -HA
110-SQFFICTAKT EWLDGKHVVF GKVKEGMNIV EAMERFGSRN G.KTSKKITI SDCGQL*  -MA
117-SQFFICTAKT EWLNGKHVVF GQVVEGMDVI KKAEAVGSSS G.RCSKPVVI ADCGQL*  -Le
111-SQFFICTVKT AWLDNKHVVF GEVEGLDVV KKIESYGSQS G.KTSKKIIV ANSGSL*  -Dm
124-SQFFICTTKC DWLDGKHYVF GRVVDGQNVV KKMESVGSKS G.KVKEPVTI SRCGELI* -SJ
107-SQFFITTAVT SWLDGKHVVF GEVESGEDVV KDMEAVGSSS G.KTSQEVLI TDCGQL*  -Eg
108-SQFFITTVPC PWLDGKHVVF GEVDGYDIV KKVESLGSPS G.ATKARIVV AKSGEL*  -Sc
  ?-SQFFLCTVKT EWLDGKHVVF GRVVEGLDVV KAVE       .KPVKDCMI ADCCQL   -Ce
```

FIG. 2C

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 1823 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:1:

```
GAATTCCGGC  GAAATAATGC  TAATTTTCTT  ATTTAATCCT  ACTATTGTGA  CGGAAAATGT       60
CAAAAAAGA   TCGCCGCCGG  GTATTTTGG   ATGTAACAAT  TGATGGTAAC  CTTGCGGGTC      120
GAATTGTGAT  GGAATTGTAC  AATGATATAG  CACCACGGAC  GTGTAATAAT  TTCCTGATGC      180
TTTGTACTGG  TATGGCAGGT  ACCGGTAAGA  TTAGTGGCAA  ACCTTTGCAC  TACAAAGGAT      240
CAACATTTCA  TCGTGTCATC  AAAAATTTCA  TGATTCAGGG  AGGTGATTTT  ACGAAAGGTG      300
ACGGTACAGG  TGGGGAATCA  ATTTATGGTG  GTATGTTTGA  CGATGAGGAA  TTCGTTATGA      360
AACATGATGA  ACCGTTTGTT  GTGTCGATGG  CGAACAAGGG  ACCTAATACG  AATGGTTCAC      420
AGTTTTTCAT  TACTACAACA  CCTGCGCCAC  ATCTCAATAA  TATCCATGTG  GTATTTGGTA      480
AGGTTGTTTC  TGGGCAGGAA  GTTGTAACCA  AAATCGAATA  TTTAAAAACT  AATTCCAAGA      540
ATCGTCCACT  AGCTGATGTT  GTAATACTTA  ATTGTGGTGA  ACTTGTTCGA  CGAAAAAAAC      600
GTCAACATTC  TTCTAGATCA  AATGAATCAG  TCAGTTCTTC  TACATCAACT  GAAAAAGTC      660
ACAAAAAGAC  AAAAAAGACA  AAAATGAAAG  AAAAGAAGCG  AAAGAGAGT   GATGAAGTGG      720
AACAATTGGA  AATTGGTACT  GTTGTTCCGG  AAGCAGAACT  GCAGTTATCG  AGCGTAAAAG      780
CTGAAGATTT  GCCTGATGAA  CCAGATCACC  AAAATAAATA  TCTTATGAGA  CGATCAAAAA      840
CGCCAGAAAA  TTCGAGGAAA  GGAAAAAAAG  AAAAGCAACG  ACAATCACCT  CATCGCTTTT      900
CGCGACGCGA  TATTGGTCAT  CGTTTGAATC  GTATGCGGAG  AACGCGAACC  GGACATAAAA      960
TAAAGGGTCG  TGGTGCACTT  AGATTTCGAA  CTCCAGAGGG  TAGTAGCGAC  CACGATGGGA     1020
GTCGTACTCC  TCCCCATTGG  AGGCGTGAAC  AGAATCGTGT  AATAACACTT  GATGAATTGC     1080
ATCGTTTGCA  AGAGAAAAGG  AAAGCATATG  AGCTTGAAGA  ACTTGAGAAT  CCCAAAAATG     1140
ATGTCGTCGA  TAAAGCAAAA  ACTGGTATAT  TATTAAACAC  ATCGGAGAAA  ATTGAAGACA     1200
AAGAGGAAAG  GTATCGCGGT  AAGTCTGAAA  AGAAGGAAAA  TCGGCATGAG  CGAAGTAGGC     1260
ATACAACGCG  ACGGTCACCG  GAGCATGTAA  CACGACATTT  TGTGAAGGAA  AAAAATCGGC     1320
ATAAAGTTGA  TGAGGTTGGG  AACAGTGAAG  ATATGAAACA  GACAAAAGA   GATCGACGAG     1380
GGCGAGCCGA  TGAAAAAGAG  AAAGTCGAAG  TTAATGGTGA  AAAAGCTGCT  GCAATGGATG     1440
AGTTAAATCT  GGATGAACCA  ACAGTAGAGG  TTACATTGGA  CAGTGCCGAA  GATATAAGAG     1500
ATAGTGATGA  CGAAGCCATT  AGGATTCATT  TATTGAAAGC  AAAAAAAATG  GCAGAAGAGA     1560
AAACGAAACA  AGAAGCAAAG  ATGCTTGAAA  AGACTGGTGA  TAAAGAAGGA  CGAGATCAAA     1620
AGACGATTTC  TGAGGCGAAA  CAGAAGGACA  GTGCTGAAAA  AGATAGGCAG  CATCGAGAGC     1680
ATAAAAATGA  TGAACTTGAA  AAGCGAGCTA  TTGAGAAACA  AGATAAAGAT  CAAATTGTAG     1740
AGAGAGATAC  AGGGAGTAAA  CAACGACGAA  AAAGTGATAG  CAAAGAACAC  AGAGAGAGAG     1800
```

AGAGAGAAAG AGAGCCGGAA TTC                                                                                             1823

(2) INFORMATION FOR SEQ ID NO:2:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:2:

Ile Pro Ala Lys
 1

(2) INFORMATION FOR SEQ ID NO:3:

(i) SEQUENCE CHARACTERISTICS:
        (A) LENGTH: 176 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:3:

```
Met Ser Lys Lys Asp Arg Arg Arg Val Phe Leu Asp Val Thr Ile Asp
 1               5                  10                  15

Gly Asn Leu Ala Gly Arg Ile Val Met Glu Leu Tyr Asn Asp Ile Ala
                20                  25                  30

Pro Arg Thr Cys Asn Asn Phe Leu Met Leu Cys Thr Gly Met Ala Gly
            35                  40                  45

Thr Gly Lys Ile Ser Gly Lys Pro Leu His Tyr Lys Gly Ser Thr Phe
        50                  55                  60

His Arg Val Ile Lys Asn Phe Met Ile Gln Gly Gly Asp Phe Thr Lys
65                  70                  75                  80

Gly Asp Gly Thr Gly Gly Glu Ser Ile Tyr Gly Gly Met Phe Asp Asp
                85                  90                  95

Glu Glu Phe Val Met Lys His Asp Glu Pro Phe Val Val Ser Met Ala
            100                 105                 110

Asn Lys Gly Pro Asn Thr Asn Gly Ser Gln Phe Phe Ile Thr Thr Thr
        115                 120                 125

Pro Ala Pro His Leu Asn Asn Ile His Val Val Phe Gly Lys Val Val
    130                 135                 140

Ser Gly Gln Glu Val Val Thr Lys Ile Glu Tyr Leu Lys Thr Asn Ser
145                 150                 155                 160

Lys Asn Arg Pro Leu Ala Asp Val Val Ile Leu Asn Cys Gly Glu Leu
                165                 170                 175
```

(2) INFORMATION FOR SEQ ID NO:4:

(i) SEQUENCE CHARACTERISTICS:
        (A) LENGTH: 176 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:4:

```
Met Gly Ala Gln Asp Arg Pro Gln Cys His Phe Asp Ile Glu Ile Asn
 1               5                  10                  15
```

```
Arg  Glu  Pro  Val  Gly  Arg  Ile  Met  Phe  Gln  Leu  Phe  Ser  Asp  Ile  Cys
               20                       25                      30

Pro  Lys  Thr  Cys  Lys  Asn  Phe  Leu  Cys  Leu  Cys  Ser  Gly  Glu  Lys  Gly
          35                       40                      45

Leu  Gly  Lys  Thr  Thr  Gly  Lys  Lys  Leu  Cys  Tyr  Lys  Gly  Ser  Thr  Phe
     50                       55                      60

His  Arg  Val  Val  Lys  Asn  Phe  Met  Ile  Gln  Gly  Gly  Asp  Phe  Ser  Glu
65                       70                       75                           80

Gly  Asn  Gly  Lys  Gly  Gly  Glu  Ser  Ile  Tyr  Gly  Gly  Tyr  Phe  Lys  Asp
               85                       90                              95

Glu  Asn  Phe  Ile  Leu  Lys  His  Asp  Arg  Ala  Phe  Leu  Leu  Ser  Met  Ala
               100                      105                     110

Asn  Arg  Gly  Lys  His  Thr  Asn  Gly  Ser  Gln  Phe  Phe  Ile  Thr  Thr  Lys
          115                      120                     125

Pro  Ala  Pro  His  Leu  Asp  Gly  Val  His  Val  Val  Phe  Gly  Leu  Val  Ile
     130                      135                     140

Ser  Gly  Phe  Glu  Val  Ile  Glu  Gln  Ile  Glu  Asn  Leu  Lys  Thr  Asp  Ala
145                      150                     155                          160

Ala  Ser  Arg  Pro  Tyr  Ala  Asp  Val  Arg  Val  Ile  Asp  Cys  Gly  Val  Leu
               165                      170                     175
```

( 2 ) INFORMATION FOR SEQ ID NO:5:

( i ) SEQUENCE CHARACTERISTICS:
        ( A ) LENGTH: 175 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:5:

```
Pro  Ser  Asn  Pro  Ser  Asn  Pro  Arg  Val  Phe  Phe  Asp  Val  Asp  Ile  Gly
1                   5                       10                      15

Gly  Glu  Arg  Val  Gly  Arg  Ile  Val  Leu  Glu  Leu  Phe  Ala  Asp  Ile  Val
               20                       25                      30

Pro  Lys  Thr  Ala  Glu  Asn  Phe  Arg  Ala  Leu  Cys  Thr  Gly  Glu  Lys  Gly
          35                       40                      45

Ile  Gly  His  Thr  Thr  Gly  Lys  Pro  Leu  His  Phe  Lys  Gly  Cys  Pro  Phe
     50                       55                      60

His  Arg  Ile  Ile  Lys  Lys  Phe  Met  Ile  Gln  Gly  Gly  Asp  Phe  Ser  Asn
65                       70                       75                           80

Gln  Asn  Gly  Thr  Gly  Gly  Glu  Ser  Ile  Tyr  Gly  Glu  Lys  Phe  Glu  Asp
               85                       90                              95

Glu  Asn  Phe  His  His  Lys  His  Asp  Arg  Glu  Gly  Leu  Leu  Ser  Met  Ala
               100                      105                     110

Asn  Ala  Gly  Arg  Asn  Thr  Asn  Gly  Ser  Gln  Phe  Phe  Ile  Thr  Thr  Val
          115                      120                     125

Pro  Thr  Pro  His  Leu  Asp  Gly  Lys  His  Val  Val  Phe  Gly  Gln  Val  Ile
     130                      135                     140

Lys  Gly  Ile  Gly  Val  Ala  Arg  Ile  Leu  Glu  Asn  Val  Glu  Val  Lys  Gly
145                      150                     155                          160

Glu  Lys  Pro  Ala  Lys  Leu  Cys  Val  Ile  Ala  Glu  Cys  Gly  Glu  Leu
               165                      170                     175
```

( 2 ) INFORMATION FOR SEQ ID NO:6:

( i ) SEQUENCE CHARACTERISTICS:
  ( A ) LENGTH: 148 amino acids
  ( B ) TYPE: amino acid
  ( C ) STRANDEDNESS: unknown
  ( D ) TOPOLOGY: unknown ( i i ) MOLECULE TYPE: protein ( x i ) SEQUENCE DESCRIPTION: SEQ ID NO:6:

```
Phe Ala Asp Ile Val Pro Lys Thr Ala Glu Asn Phe Arg Ala Leu Cys
1               5                   10                  15

Thr Gly Glu Lys Gly Ile Gly Pro Thr Thr Gly Lys Pro Leu His Phe
            20                  25                  30

Lys Gly Cys Pro Phe His Arg Ile Ile Lys Lys Phe Met Ile Gln Gly
        35                  40                  45

Gly Asp Phe Ser Asn Gln Asn Gly Thr Gly Gly Glu Ser Ile Tyr Gly
    50                  55                  60

Glu Lys Phe Glu Asp Glu Asn Phe His Tyr Lys His Asp Lys Glu Gly
65                  70                  75                  80

Leu Leu Ser Met Ala Asn Ala Gly Ser Asn Thr Asn Gly Ser Gln Phe
                85                  90                  95

Phe Ile Thr Thr Val Pro Thr Pro His Leu Asp Gly Lys His Val Val
            100                 105                 110

Phe Gly Gln Val Xaa Lys Gly Met Gly Val Ala Lys Ile Leu Glu Asn
        115                 120                 125

Val Glu Val Lys Gly Glu Lys Pro Ala Lys Leu Cys Val Ile Ala Glu
    130                 135                 140

Cys Gly Glu Leu
145
```

( 2 ) INFORMATION FOR SEQ ID NO:7:

( i ) SEQUENCE CHARACTERISTICS:
    ( A ) LENGTH: 169 amino acids
    ( B ) TYPE: amino acid
    ( C ) STRANDEDNESS: unknown
    ( D ) TOPOLOGY: unknown ( i i ) MOLECULE TYPE: protein ( x i ) SEQUENCE DESCRIPTION: SEQ ID NO:7:

```
Met Ala His Cys Phe Phe Asp Met Thr Ile Gly Gly Gln Pro Ala Gly
1               5                   10                  15

Arg Ile Ile Met Glu Leu Phe Pro Asp Val Pro Lys Thr Ala Glu Asn
            20                  25                  30

Phe Arg Ala Leu Cys Thr Gly Glu Lys Gly Ile Gly Pro Ser Gly Lys
        35                  40                  45

Lys Met Thr Tyr Glu Gly Ser Val Phe His Arg Val Ile Pro Lys Phe
    50                  55                  60

Met Leu Gln Gly Gly Asp Phe Thr Leu Gly Asn Gly Arg Gly Gly Glu
65                  70                  75                  80

Ser Ile Tyr Gly Ala Lys Phe Ala Asp Glu Asn Phe Ile His Lys His
                85                  90                  95

Thr Thr Pro Gly Leu Leu Ser Met Ala Asn Ala Gly Pro Gly Thr Asn
            100                 105                 110

Gly Ser Gln Phe Phe Ile Thr Thr Val Ala Thr Pro His Leu Asp Gly
        115                 120                 125

Lys His Val Val Phe Gly Lys Val Val Glu Gly Met Asp Val Val Arg
```

|     |     |     | 130 |     |     |     | 135 |     |     |     | 140 |     |     |     |
| --- | --- | --- | --- | --- | --- | --- | --- | --- | --- | --- | --- | --- | --- | --- |
| Lys | Ile | Glu | Ala | Thr | Gln | Thr | Asp | Arg | Gly | Asp | Lys | Pro | Leu | Ser | Glu |
| 145 |     |     |     |     | 150 |     |     |     |     | 155 |     |     |     |     | 160 |
| Val | Lys | Ile | Ala | Lys | Cys | Gly | Gln | Leu |
|     |     |     |     | 165 |

( 2 ) INFORMATION FOR SEQ ID NO:8:

( i ) SEQUENCE CHARACTERISTICS:
        ( A ) LENGTH: 165 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:8:

| Met | Val | Asn | Pro | Thr | Val | Phe | Phe | Asp | Ile | Ala | Val | Asp | Gly | Glu | Pro |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |
| Leu | Gly | Arg | Val | Ser | Phe | Glu | Leu | Phe | Ala | Asp | Lys | Val | Pro | Lys | Thr |
|     |     |     | 20 |     |     |     |     | 25 |     |     |     |     | 30 |     |     |
| Ala | Glu | Asn | Phe | Arg | Ala | Leu | Ser | Thr | Gly | Glu | Lys | Gly | Phe | Gly | Tyr |
|     |     | 35 |     |     |     |     | 40 |     |     |     |     | 45 |     |     |     |
| Lys | Gly | Ser | Cys | Phe | His | Arg | Ile | Ile | Pro | Gly | Phe | Met | Cys | Gln | Gly |
|     | 50 |     |     |     |     | 55 |     |     |     |     |     | 60 |     |     |     |
| Gly | Asp | Phe | Thr | Arg | His | Asn | Gly | Thr | Gly | Gly | Lys | Ser | Ile | Tyr | Gly |
| 65 |     |     |     |     | 70 |     |     |     |     | 75 |     |     |     |     | 80 |
| Glu | Lys | Phe | Glu | Asp | Glu | Asn | Phe | Ile | Leu | Lys | His | Thr | Gly | Pro | Gly |
|     |     |     |     | 85 |     |     |     |     | 90 |     |     |     |     | 95 |     |
| Ile | Leu | Ser | Met | Ala | Asn | Ala | Gly | Pro | Asn | Thr | Asn | Gly | Ser | Gln | Phe |
|     |     |     | 100 |     |     |     |     | 105 |     |     |     |     | 110 |     |     |
| Phe | Ile | Cys | Thr | Ala | Lys | Thr | Glu | Trp | Leu | Asp | Gly | Lys | His | Val | Val |
|     |     | 115 |     |     |     |     | 120 |     |     |     |     | 125 |     |     |     |
| Phe | Gly | Lys | Val | Lys | Glu | Gly | Met | Asn | Ile | Val | Glu | Ala | Met | Glu | Arg |
|     | 130 |     |     |     |     | 135 |     |     |     |     | 140 |     |     |     |     |
| Phe | Gly | Ser | Arg | Asn | Gly | Lys | Thr | Ser | Lys | Lys | Ile | Thr | Ile | Ala | Asp |
| 145 |     |     |     |     | 150 |     |     |     |     | 155 |     |     |     |     | 160 |
| Cys | Gly | Gln | Leu | Glu |
|     |     |     |     | 165 |

( 2 ) INFORMATION FOR SEQ ID NO:9:

( i ) SEQUENCE CHARACTERISTICS:
        ( A ) LENGTH: 164 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:9:

| Met | Val | Asn | Pro | Thr | Val | Phe | Phe | Asp | Ile | Thr | Ala | Asp | Asp | Glu | Pro |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |
| Leu | Gly | Arg | Val | Ser | Phe | Glu | Leu | Phe | Ala | Asp | Lys | Val | Pro | Lys | Thr |
|     |     |     | 20 |     |     |     |     | 25 |     |     |     |     | 30 |     |     |
| Ala | Glu | Asn | Phe | Arg | Ala | Leu | Ser | Thr | Gly | Glu | Lys | Gly | Phe | Gly | Tyr |
|     |     | 35 |     |     |     |     | 40 |     |     |     |     | 45 |     |     |     |
| Lys | Gly | Ser | Ser | Phe | His | Arg | Ile | Ile | Pro | Gly | Phe | Met | Cys | Gln | Gly |
|     | 50 |     |     |     |     | 55 |     |     |     |     |     | 60 |     |     |     |

| Gly<br>65 | Asp | Phe | Thr | Arg | His<br>70 | Asn | Gly | Thr | Gly<br>75 | Gly | Arg | Ser | Ile | Tyr<br>80 | Gly |
|---|---|---|---|---|---|---|---|---|---|---|---|---|---|---|---|
| Glu | Lys | Phe | Glu | Asp<br>85 | Glu | Asn | Phe | Ile | Leu<br>90 | Lys | His | Thr | Gly | Pro<br>95 | Gly |
| Ile | Leu | Ser | Met<br>100 | Ala | Asn | Ala | Gly | Pro<br>105 | Asn | Thr | Asn | Gly | Ser<br>110 | Gln | Phe |
| Phe | Ile | Cys<br>115 | Thr | Ala | Lys | Thr | Glu<br>120 | Trp | Leu | Asp | Gly | Lys<br>125 | His | Val | Val |
| Phe | Gly<br>130 | Lys | Val | Lys | Glu | Gly<br>135 | Met | Asn | Ile | Val | Glu<br>140 | Ala | Met | Glu | Arg |
| Phe<br>145 | Gly | Ser | Arg | Asn | Gly<br>150 | Lys | Thr | Ser | Lys | Lys<br>155 | Ile | Thr | Ile | Ser | Asp<br>160 |
| Cys | Gly | Gln | Leu | | | | | | | | | | | | |

(2) INFORMATION FOR SEQ ID NO:10:

(i) SEQUENCE CHARACTERISTICS:
        (A) LENGTH: 171 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:10:

| Met<br>1 | Ala | Asn | Pro | Lys<br>5 | Val | Phe | Phe | Asp | Leu<br>10 | Thr | Ile | Gly | Gly | Ala<br>15 | Pro |
|---|---|---|---|---|---|---|---|---|---|---|---|---|---|---|---|
| Ala | Gly | Arg | Val<br>20 | Val | Met | Glu | Leu | Phe<br>25 | Ala | Asp | Thr | Thr | Pro<br>30 | Lys | Thr |
| Ala | Glu | Asn<br>35 | Phe | Arg | Ala | Leu | Cys<br>40 | Thr | Gly | Glu | Lys | Gly<br>45 | Val | Gly | Lys |
| Met | Gly<br>50 | Lys | Pro | Leu | His | Tyr<br>55 | Lys | Gly | Ser | Thr | Phe<br>60 | His | Arg | Val | Ile |
| Pro<br>65 | Gly | Phe | Met | Cys | Gln<br>70 | Gly | Gly | Asp | Phe | Thr<br>75 | Ala | Gly | Asn | Gly | Thr<br>80 |
| Gly | Gly | Glu | Ser | Ile<br>85 | Tyr | Gly | Ala | Lys | Phe<br>90 | Asn | Asp | Glu | Asn | Phe<br>95 | Val |
| Lys | Lys | His | Thr<br>100 | Gly | Pro | Gly | Ile | Leu<br>105 | Ser | Met | Ala | Asn | Ala<br>110 | Gly | Pro |
| Gly | Thr | Asn<br>115 | Gly | Ser | Gln | Phe | Phe<br>120 | Ile | Cys | Thr | Ala | Lys<br>125 | Thr | Glu | Trp |
| Leu | Asn<br>130 | Gly | Lys | His | Val | Val<br>135 | Phe | Gly | Gln | Val | Val<br>140 | Glu | Gly | Met | Asp |
| Val<br>145 | Ile | Lys | Lys | Ala | Glu<br>150 | Ala | Val | Gly | Ser | Ser<br>155 | Ser | Gly | Arg | Cys | Ser<br>160 |
| Lys | Pro | Val | Val | Ile<br>165 | Ala | Asp | Cys | Gly | Gln<br>170 | Leu | | | | | |

(2) INFORMATION FOR SEQ ID NO:11:

(i) SEQUENCE CHARACTERISTICS:
        (A) LENGTH: 165 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:11:

```
Met Ser Thr Leu Pro Arg Val Phe Phe Asp Met Thr Ala Asp Asn Glu
1               5                   10                  15

Pro Leu Gly Arg Ile Val Met Glu Leu Arg Ser Asp Val Val Pro Lys
                20              25                  30

Thr Ala Glu Asn Phe Arg Ala Leu Cys Thr Gly Glu Lys Gly Phe Gly
            35              40              45

Tyr Lys Gly Ser Ile Phe His Arg Val Ile Pro Asn Phe Met Cys Gln
    50              55              60

Gly Gly Asp Phe Thr Asn His Asn Gly Thr Gly Lys Ser Ile Tyr
65              70              75                      80

Gly Asn Lys Phe Pro Asp Glu Asn Phe Glu Leu Lys His Thr Gly Ser
                85              90                  95

Gly Ile Leu Ser Met Ala Asn Ala Gly Ala Asn Thr Asn Gly Ser Gln
            100             105             110

Phe Phe Ile Cys Thr Val Lys Thr Ala Trp Leu Asp Asn Lys His Val
        115             120             125

Val Phe Gly Glu Val Val Glu Gly Leu Asp Val Val Lys Lys Ile Glu
    130             135             140

Ser Tyr Gly Ser Gln Ser Gly Lys Thr Ser Lys Lys Ile Ile Val Ala
145             150             155                     160

Asn Ser Gly Ser Leu
                165
```

( 2 ) INFORMATION FOR SEQ ID NO:12:

( i ) SEQUENCE CHARACTERISTICS:
        ( A ) LENGTH: 168 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:12:

```
Lys Gln Lys Arg Asn Leu Pro Arg Val Phe Phe Asp Ile Arg Ile Gly
1               5                   10                  15

Asn Ala Asp Arg Gly Arg Ile Val Met Glu Leu Arg Ser Asp Ile Val
                20              25                  30

Pro Arg Thr Ala Glu Asn Phe Arg Ala Leu Cys Thr Gly Asp Arg Gly
            35              40              45

Phe Gly Tyr His Asn Cys Cys Phe His Arg Val Ile Pro Gln Phe Met
    50              55              60

Cys Gln Gly Gly Asp Phe Val Lys Gly Asp Gly Thr Gly Gly Lys Ser
65              70              75                      80

Ile Tyr Gly Arg Lys Phe Asp Asp Glu Asn Phe Gln Leu Arg His Glu
                85              90                  95

Gly Phe Gly Val Leu Ser Met Ala Asn Ser Gly Pro Asn Thr Asn Gly
            100             105             110

Ser Gln Phe Phe Ile Cys Thr Thr Lys Cys Asp Trp Leu Asp Gly Lys
        115             120             125

His Tyr Val Phe Gly Arg Val Val Asp Gly Gln Asn Val Val Lys Lys
    130             135             140

Met Glu Ser Val Gly Ser Lys Ser Gly Lys Val Lys Glu Pro Val Thr
145             150             155                     160

Ile Ser Arg Cys Gly Glu Leu Ile
                165
```

( 2 ) INFORMATION FOR SEQ ID NO:13:

( i ) SEQUENCE CHARACTERISTICS:
        ( A ) LENGTH: 161 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:13:

```
Gly Val Lys Cys Phe Phe Asp Ile Ser Ile Gly Gly Lys Pro Ala Gly
  1           5                  10                  15
Arg Ile Val Phe Ala Leu Phe Asp Asp Val Pro Lys Thr Val Glu Asn
             20                  25                  30
Phe Arg Ala Leu Cys Thr Gly Glu Lys Gly Phe Gly Tyr Lys Gly Ser
         35                  40                  45
Lys Phe His Arg Ile Ile Pro Gly Phe Met Cys Gln Gly Gly Asp Phe
     50                  55                  60
Thr Ala Gly Asn Gly Thr Gly Gly Lys Ser Ile Tyr Gly Ser Lys Phe
 65                  70                  75                  80
Glu Asp Glu Asn Phe Asn His Lys His Ser Lys Pro Met Met Leu Ser
                 85                  90                  95
Met Ala Asn Ala Gly Lys Asn Thr Asn Gly Ser Gln Phe Phe Ile Thr
                100                 105                 110
Thr Ala Val Thr Ser Trp Leu Asp Gly Lys His Val Val Phe Gly Glu
            115                 120                 125
Val Glu Ser Gly Glu Asp Val Val Lys Asp Met Glu Ala Val Gly Ser
    130                 135                 140
Ser Ser Gly Lys Thr Ser Gln Glu Val Leu Ile Thr Asp Cys Gly Gln
145                 150                 155                 160
Leu
```

( 2 ) INFORMATION FOR SEQ ID NO:14:

( i ) SEQUENCE CHARACTERISTICS:
        ( A ) LENGTH: 162 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:14:

```
Met Ser Gln Val Tyr Phe Asp Val Glu Ala Asp Gly Gln Pro Ile Gly
  1           5                  10                  15
Arg Val Val Phe Lys Leu Tyr Asn Asp Ile Val Pro Lys Thr Ala Glu
             20                  25                  30
Asn Phe Arg Ala Leu Cys Thr Gly Glu Lys Gly Phe Gly Tyr Ala Gly
         35                  40                  45
Ser Pro Phe His Arg Val Ile Pro Asp Phe Met Leu Gln Gly Gly Asp
     50                  55                  60
Phe Thr Ala Gly Asn Gly Thr Gly Gly Lys Ser Ile Tyr Gly Gly Lys
 65                  70                  75                  80
Phe Pro Asp Glu Asn Phe Lys Lys His His Asp Arg Pro Gly Leu Leu
                 85                  90                  95
Ser Met Ala Asn Ala Gly Pro Asn Thr Asn Gly Ser Gln Phe Phe Ile
                100                 105                 110
```

-continued

```
Thr Thr Val Pro Cys Pro Trp Leu Asp Gly Lys His Val Val Phe Gly
    115             120                 125

Glu Val Val Asp Gly Tyr Asp Ile Val Lys Lys Val Glu Ser Leu Gly
    130             135                 140

Ser Pro Ser Gly Ala Thr Lys Ala Arg Ile Val Val Ala Lys Ser Gly
145             150                 155                 160

Glu Leu
```

( 2 ) INFORMATION FOR SEQ ID NO:15:

( i ) SEQUENCE CHARACTERISTICS:
        ( A ) LENGTH: 109 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:15:

```
Arg Asp Pro Ile Phe Xaa Arg Ile Ile Pro Asn Phe Met Xaa Gln Gly
1               5                   10                  15

Gly Asp Phe Thr Arg Gly Asn Gly Thr Gly Gly Glu Ser Ile Tyr Gly
            20                  25                  30

Glu Lys Phe Pro Asp Glu Asn Phe Lys Glu Lys His Thr Gly Pro Gly
        35                  40                  45

Val Leu Ser Met Ala Asn Ala Gly Pro Asn Thr Asn Gly Ser Gln Phe
    50                  55                  60

Phe Leu Cys Thr Val Lys Thr Glu Trp Leu Asp Gly Lys His Val Val
65              70                  75                  80

Phe Gly Arg Val Val Glu Gly Leu Asp Val Val Lys Ala Val Glu Lys
                85                  90                  95

Pro Val Lys Asp Cys Met Ile Ala Asp Cys Cys Gln Leu
            100                 105
```

( 2 ) INFORMATION FOR SEQ ID NO:16:

( i ) SEQUENCE CHARACTERISTICS:
        ( A ) LENGTH: 28 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:16:

GGGGATCCAT GTCAAAAAAA GATCGGCG                      28

( 2 ) INFORMATION FOR SEQ ID NO:17:

( i ) SEQUENCE CHARACTERISTICS:
        ( A ) LENGTH: 32 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:17:

CGGAAGCTTC AGAATTCCGG CTCTCTTTCT CT                 32

( 2 ) INFORMATION FOR SEQ ID NO:18:

( i ) SEQUENCE CHARACTERISTICS:

( A ) LENGTH: 22 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:18:

GGTGGTATGT TTGACGATGA GC 22

( 2 ) INFORMATION FOR SEQ ID NO:19:

( i ) SEQUENCE CHARACTERISTICS:
( A ) LENGTH: 22 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:19:

CAACCTTACC AAATACCACA TG 22

( 2 ) INFORMATION FOR SEQ ID NO:20:

( i ) SEQUENCE CHARACTERISTICS:
( A ) LENGTH: 8 amino acids
( B ) TYPE: amino acid
( D ) TOPOLOGY: linear ( i i ) MOLECULE TYPE: protein ( x i ) SEQUENCE DESCRIPTION: SEQ ID NO:20:

Phe Ser Tyr Leu Ile Leu Leu Leu
1               5

( 2 ) INFORMATION FOR SEQ ID NO:21:

( i ) SEQUENCE CHARACTERISTICS:
( A ) LENGTH: 591 amino acids
( B ) TYPE: amino acid
( D ) TOPOLOGY: linear ( i i ) MOLECULE TYPE: protein ( x i ) SEQUENCE DESCRIPTION: SEQ ID NO:21:

Arg Lys Met Ser Lys Lys Asp Arg Arg Val Phe Leu Asp Val Thr
1               5                   10                  15

Ile Asp Gly Asn Leu Ala Gly Arg Ile Val Met Glu Leu Tyr Asn Asp
            20                  25                  30

Ile Ala Pro Arg Thr Cys Asn Asn Phe Leu Met Leu Cys Thr Gly Met
                35              40              45

Ala Gly Thr Gly Lys Ile Ser Gly Lys Pro Leu His Tyr Lys Gly Ser
        50              55              60

Thr Phe His Arg Val Ile Lys Asn Phe Met Ile Gln Gly Gly Asp Phe
65              70              75              80

Thr Lys Gly Asp Gly Thr Gly Gly Glu Ser Ile Tyr Gly Gly Met Phe
            85              90              95

Asp Asp Glu Glu Phe Val Met Lys His Asp Glu Pro Phe Val Val Ser
            100             105             110

Met Ala Asn Lys Gly Pro Asn Thr Asn Gly Ser Gln Phe Phe Ile Thr
            115             120             125

Thr Thr Pro Ala Pro His Leu Asn Asn Ile His Val Val Phe Gly Lys
        130             135             140

```
Val  Val  Ser  Gly  Gln  Glu  Val  Val  Thr  Lys  Ile  Glu  Tyr  Leu  Lys  Thr
145            150                 155                                    160

Asn  Ser  Lys  Asn  Arg  Pro  Leu  Ala  Asp  Val  Val  Ile  Leu  Asn  Cys  Gly
                    165                      170                      175

Glu  Leu  Val  Arg  Arg  Lys  Lys  Arg  Gln  His  Ser  Ser  Arg  Ser  Asn  Glu
               180                      185                      190

Ser  Val  Ser  Ser  Ser  Thr  Ser  Thr  Glu  Lys  Ser  His  Lys  Lys  Thr  Lys
               195                 200                      205

Lys  Thr  Lys  Met  Lys  Glu  Lys  Lys  Arg  Lys  Glu  Ser  Asp  Glu  Val  Glu
          210                 215                      220

Gln  Leu  Glu  Ile  Gly  Thr  Val  Val  Pro  Glu  Ala  Glu  Leu  Gln  Leu  Ser
225                      230                 235                           240

Ser  Val  Lys  Ala  Glu  Asp  Leu  Pro  Asp  Glu  Pro  Asp  His  Gln  Asn  Lys
                    245                 250                           255

Tyr  Leu  Met  Arg  Arg  Ser  Lys  Thr  Pro  Glu  Asn  Ser  Arg  Lys  Gly  Lys
               260                 265                      270

Lys  Glu  Lys  Gln  Arg  Gln  Ser  Pro  His  Arg  Phe  Ser  Arg  Arg  Asp  Ile
          275                 280                      285

Gly  His  Arg  Leu  Asn  Arg  Met  Arg  Arg  Thr  Arg  Thr  Gly  His  Lys  Ile
     290                      295                 300

Lys  Gly  Arg  Gly  Ala  Leu  Arg  Phe  Arg  Thr  Pro  Glu  Gly  Ser  Ser  Asp
305                      310                 315                           320

His  Asp  Gly  Ser  Arg  Thr  Pro  Pro  His  Trp  Arg  Arg  Glu  Gln  Asn  Arg
               325                      330                      335

Val  Ile  Thr  Leu  Asp  Glu  Leu  His  Arg  Leu  Gln  Glu  Lys  Arg  Lys  Ala
               340                      345                      350

Tyr  Glu  Leu  Glu  Glu  Leu  Glu  Asn  Pro  Lys  Asn  Asp  Val  Val  Asp  Lys
               355                      360                 365

Ala  Lys  Thr  Gly  Ile  Leu  Leu  Asn  Thr  Ser  Glu  Lys  Ile  Glu  Asp  Lys
     370                      375                 380

Glu  Glu  Arg  Tyr  Arg  Gly  Lys  Ser  Glu  Lys  Lys  Glu  Asn  Arg  His  Glu
385                      390                 395                           400

Arg  Ser  Arg  His  Thr  Thr  Arg  Arg  Ser  Pro  Glu  His  Val  Thr  Arg  His
               405                      410                      415

Phe  Val  Lys  Glu  Lys  Asn  Arg  His  Lys  Val  Asp  Glu  Val  Gly  Asn  Ser
                    420                 425                      430

Glu  Asp  Met  Lys  Gln  Thr  Lys  Arg  Asp  Arg  Arg  Gly  Arg  Ala  Asp  Glu
               435                 440                      445

Lys  Glu  Lys  Val  Glu  Val  Asn  Gly  Glu  Lys  Ala  Ala  Ala  Met  Asp  Glu
     450                 455                      460

Leu  Asn  Leu  Asp  Glu  Pro  Thr  Val  Glu  Val  Thr  Leu  Asp  Ser  Ala  Glu
465                      470                 475                           480

Asp  Ile  Arg  Asp  Ser  Asp  Asp  Glu  Ala  Ile  Arg  Ile  His  Leu  Leu  Lys
               485                      490                      495

Ala  Lys  Lys  Met  Ala  Glu  Glu  Lys  Thr  Lys  Gln  Glu  Ala  Lys  Met  Leu
               500                 505                      510

Glu  Lys  Thr  Gly  Asp  Lys  Glu  Gly  Arg  Asp  Gln  Lys  Thr  Ile  Ser  Glu
          515                      520                 525

Ala  Lys  Gln  Lys  Asp  Ser  Ala  Glu  Lys  Asp  Arg  Gln  His  Arg  Glu  His
     530                 535                      540

Lys  Asn  Asp  Glu  Leu  Glu  Lys  Arg  Ala  Ile  Glu  Lys  Gln  Asp  Lys  Asp
545                 550                      555                           560
```

-continued

```
Gln  Ile  Val  Glu  Arg  Asp  Thr  Gly  Ser  Lys  Gln  Arg  Arg  Lys  Ser  Asp
               565                      570                     575

Ser  Lys  Glu  His  Arg  Glu  Arg  Glu  Arg  Glu  Arg  Glu  Pro  Glu  Phe
               580                      585                     590
```

METHOD FOR IDENTIFYING ANTI-PARASITIC COMPOUNDS

BACKGROUND OF THE INVENTION

The present invention relates a method for identifying anti-parasitic compounds. More specifically, the present invention relates to a method for the identification of compounds capable of binding and/or inhibiting cyclophilin-like proteins, as well as to methods of treating parasitic infections which are not susceptible to cyclosporin A.

Cyclophilin is a common protein, which by definition, binds avidly to the immunosuppressive agent cyclosporin A (CsA). CsA is a fungal cyclic undecapeptide, which at present is a widely used therapeutic agent for the prevention of graft rejection. This drug is therefore preferentially used in kidney, liver, heart and bone marrow transplantation, and in the treatment of various autoimmune diseases [Kahn, *Cyclosporin: Biological Activity And Clinical Applications* Grune & Stratton, Orlando, FL (1983)].

Cyclophilin has recently been shown to posses peptidyl-prolyl cis-trans isomerase (PPiase) or rotamase activity [Fischer, et al., *Nature,* 337:476–478 (1989)], and CsA has been demonstrated to actively inhibit this enzymatic activity [Takahashi, et al, *Nature,* 337:473–475 (1989)]. This enzyme catalyzes the cis-trans isomerization of proline-imidic peptide bonds in oligopeptides and has been demonstrated to accelerate the refolding of several proteins, including collagens [Bachinger, *J. Biol. Chem.,* 262:17144–17148 (1987)]. In addition to actively inhibiting PPiase activity, [Takahashi, et al., *Nature,* 337:473– 475 (1989)] CsA has been demonstrated to slow down the in vitro folding of collagen triple helices [Steinmann, et al., *J. Biol. Chem.,* 266:1299–1303 (1991)]. Not all cyclophilins bind CsA to the same degree. In a study involving *E. coil* and human cyclophilins, it has been clearly shown that the major determinant in the binding of CsA by cyclophilin is a tryptophan residue in the drug binding domain [Lui, et al., *Biochemistry,* 30:2306–2310 (1991)]. It also been shown that cyclophilins in which this tryptophan residue has been substituted by another amino acid will not bind to CsA [(Kieffer, et al., *J. Biol. Chem.* 267:5503–5507 (1992)].

Investigators have only recently been able to elucidate the mode of action of both CsA, and the functionally, but not chemically related immunosuppressant FK-506 on T-cells. The PPiase activity of both cyclophilin and the FK-506 receptor FKBP are now not believed to be involved in its immunosuppressive action. It is currently hypothesized that CsA and FK-506 bind to endogenous cytosolic cyclophilin or FKBP to form a complex which can subsequently bind to calcineurin, therefore inhibiting dephosphorylation and preventing access to transcription factors such as NF-AT into the nucleus of the T-cell [Schreiber & Crabtree, *Immunol. Today,* 13:136–142 (1992)].

CsA has also been demonstrated as having broad spectrum anti-parasite effects [Chappell & Wastling, *Parasitol.,* 105:S25–S40 (1992)]. Parasitic protozoa affected, include *Leishmania major* [(Behforouz, et al, *J. Immunol,* 136:3067–3075 (1986)] and Plasmodium species [Nickell, et al., *Infect. & Immunol.,* 37:1093–1100 (1982); Thommen-Scott, *Agents & Actions,* 11:770–773 (1981)]. Susceptible helminth parasites include the trematode parasites *Schistosoma mansoni* [(Nilsson, et al, *Parasitol. Immunol.,* 7:19–27 (1985); Pons, et al, *Exper. Parasitol,* 67:190–198 (1988); Munro & McLaren, *Parasitol.,* 100:19–29 (1990a) and Munro & McLaren, *Parasitol.,* 100:29–34 (1990b)] and *Paragonimus miyazakii* [Hashiguchi & Okamura, *J. Helminthol,* 62:251–256 (1988)], the cestode species *Hymenolepis microstoma* [Wastling, et al., *Parasitol.,* 104:531–538 (1992)]. Nematode species affected by CsA include *Acanthocheilonema vitae* [Bout, et al., *Trans. Roy. Soc. Trop. Med. Hyg.,* 78:670–671 (1984)], *Litomosoides carinii* [Zahner & Schultheiss, *J. Helminthol.,* 61:282–290 (1987)]and *Trichinella spiralis* [Bolas-Fernandez, et al, *Parasit. Immunol.,* 10:111–116 (1988)]. In one example, CsA administered to the host at sub-immunosuppressive levels prior to *S. mansoni* infections, was demonstrated as exerting profound Schistosomicidal effects, causing gross herniation of the parasites gut and blistering of the tegumental surface [Munro & McLaren, *Parasitol.,* 100:19–29 (1990a)]. These effects have also been demonstrated in vitro with both *S. mansoni* and *Fasciola hepatica* [Chappel, et al., *Parasitology,* in press (1993)], therefore ruling out the possibility of CsA exerting an indirect effect via the host. Interestingly cyclophilin has been identified in *S. mansoni* [Koletsky, *J. Immunol.,* 137:1054–1059 (1986)], and has recently been cloned from the closely-related trematode *S. japonicum* [Argaet & Mitchell, *J. Parasitol.,* 78:660–664 (1992)] using a probe corresponding to the cyclophilin gene from the cestode parasite *Echinococcus granulous* [Lightowlers, et al., *Mol. Biochem. Parasitol.,* 36:287–290 (1989)].

CsA anti-nematode effects include the reduction in the microfilarial levels in rodents infected with *L. carinii* [Zahner, et al., *J. Helminthol.,* 61:282–290 (1987)], killing of *A. vitae* in rodents [Bout, et al., *Trans Roy. Soc. Trop. Med. Hyg.,* 78:670–671 (1984)]. In the adenophorean nematode *T. spiralis,* treatment of infected mice with this drug resulted in a significant reduction of muscle stage larvae [Bolas-Fernandez, et al., *Parasit. Immunol.,* 10:111–116 (1988)]. In common between the anti-nematode effects of this drug are its selective effects against early larval stages, with general resistance of reduced susceptibility in the later adult stages.

However, not all parasites have been found to be susceptible to the effects of CsA. For example, in *Brugia pahangi,* CsA showed no effect on either adults or microfilarial levels [Lawrence et al., *Parasit. Immunol.* 14:371(1992)]. It would therefore be desirable to have a compound that could be used to treat parasites which are not susceptible to the anti-parasitic effects of CsA.

It would be desirable to have a method which can be used to readily screen and select compounds that are capable of binding cyclophilins from parasites which are not susceptible to the anti-parasitic effects of CsA and/or which inhibit the PPiase activity of such proteins. More specifically, it would be desirable to have a method which can be used to screen and select CsA derivatives that are capable of binding such cyclophilins and inhibiting PPiase activity while having reduced immunosuppressive activity on the host.

SUMMARY OF THE INVENTION

In accordance with the present invention, it has been discovered that parasites which are not susceptible to the anti-parasitic effects of CsA, possess cyclophilins in which the conserved tryptophan at the CsA binding domain has been substituted with another amino acid, in particular substituted with histidine. The present invention relates to the use of these cyclophilins, hereinafter referred to as "cyclophilin-like proteins (CLP)", in a method for identifying compounds capable of binding to and/or inhibiting the enzymatic activity of these proteins. Such compounds may be further screened for their ability to inhibit parasites which are not susceptible to the anti-parasitic effects of CsA.

Generally, this method comprises contacting a cyclophilin-like protein with a compound to be tested (test compound) and measuring the change in enzymatic activity. Preferably, the test compound is a CsA derivative. Most preferably, the CsA derivative is a binding site derivative. In particular, this method can be used to screen for CsA derivatives capable of binding to filarial cyclophilin-like proteins that inhibit PPiase activity and/or are less or non-immunosuppressive to the host.

In a preferred embodiment, a fusion protein comprising the CLP and protein having binding affinity for a substrate, e.g., malE, is used in an affinity chromatography system to screen and select binding compounds. In this method, the fusion protein is contacted with a substrate to which the binding protein has specific affinity such that the fusion protein is reversibly affixed to the column. A test compound is then added to the column. The compound may be labeled. The column is then washed and analyzed to determine the presence of the compounds. Compounds found to have binding affinity for the fusion protein can then be tested for the ability to inhibit PPiase activity.

One cyclophilin-like protein useful in the method of the present invention is from a parasitic nematode, the human filarial parasite B. malayi.

The present invention further relates to the use the DNA encoding the B. malayi cyclophilin-like protein, or a fragment thereof, in the identification and isolation of related genes from other organisms, including other species of parasitic nematodes. Using the DNA encoding the B. malayi CLP as a nucleotide probe in a Southern blot, the present inventors have determined the presence of related genes in the parasites Brugia pahangi, Dirofilaria immitis, Acanthocheilonema vitae, Litomosoides carinii, and Onchocerca gibsoni.

BRIEF DESCRIPTION OF THE DRAWINGS

FIG. 1 is the nucleotide (SEQ ID NO:1) and deduced amino acid sequence (amino acids 17-607) (SEQ ID NO:21) of B. malayi cyclophilin. Amino acids 1-4 and 8-15 are represented in the Sequence Listing as SEQ ID NO:2 and SEQ ID NO:20, respectively. The cyclophilin domain is underlined.

FIG. 2 is the amino acid alignment of cyclophilins from eukaryotes. Sequences were aligned against the Brugia malayi cyclophilin (Bm (SEQ ID NO: 3)) using the Gap program, sequences were taken from Hnk-human natural killer cell (SEQ ID NO:4) [Anderson, et al, Proc. Natl. Acad. Sci. USA, 90:542–546 (1993)], 60% identical, (gp:L04288); H40-human cyclophilin-40 (SEQ ID NO:5) [Kieffer, et al., J. Biol. Chem., 268:12303–12310 (1993)], 56% identical, (gp:L11667); B40-bovine cyclophilin-40 (SEQ ID NO:6) [Kieffer, et al., supra (1993)], 57% identical (gp:L11668); AT-Arabidopsis thaliana (SEQ ID NO:7) [Bartling, et al, Plant Mol. Biol., 19:529–530 (1992)], 61% identical (gp:X63616); HA-human cyclophilin A (SEQ ID NO:8) [Haendler, et al, EMBO J., 6:947–950 (1987)], 59% identical (gp:X52851]; MA-mouse cyclophilin A (SEQ ID NO:9) [Hasel & Sutcliffe, Nucleic Acids Res., 18:4019 (1990)], 59% identical (gp:X52851); Le-Lycopersicon esculentum (SEQ ID NO:10) [Gasser, et al., Proc. Natl. Acad. Sci. USA, 87:9519–9523 (1990)], 65% identical (pir:A39252); Dm-Drosophila melanogaster cyclophilin A (SEQ ID NO:11) [Stamnes, et al., Cell, 65:219–227 (1991)], 63% identical (gp:M62398); Sj-Schistosoma japonicum (SEQ ID NO:12) [Argaet & Mitchell, J. Parasitol., 78:660–664 (1992)], 61% identical (gp:M93420); Eg-Echinococcus granulosus (SEQ ID NO:13) [Lightowlers, et al., Mol. Bio. Chem. Parasitol., 36:287–290 (1989)], 58% identical [gp:J04664); Sc-Saccharomyces cerevisae cyclophilin A (SEQ ID NO:14) [Haendler, et al., Gene, 83:39–46 (1989)], 63% identical (gp:X17505); and Ce-Caenorhabditis elegans (SEQ ID NO:15) [McCombie, et al., Nature Genet., 1:124–131 (1992)], 60% identical (gb:CELXT00178). The residues important in CsA binding [Ke, et al., Proc. Natl. Acad. Sci., USA,, 88:9483–9847 (1993)] are blocked and the residues having identity with Brugia malayi are highlighted.

FIG. 3A shows B. malayi L4 from host treated with Csa (magnification ×14,560);

FIG. 3B shows B. malayi adults from host treated with CsA (magnification ×24,000); and FIG. 3C shows B. malayi adults from a control host (magnification ×30,000).

FIG. 4A shows C. elegans with no CsA (magnification × 17,600);

FIG. 4B shows C. elegans with 10 µg Csa (magnification × 9,120);

FIG. 4C shows C. elegans with 100 µg Csa (magnification × 11,360); and

FIG. 4D shows C. elegans with 500 µg Csa (magnification × 11,360).

DETAILED DESCRIPTION OF THE INVENTION

Figure 3A:
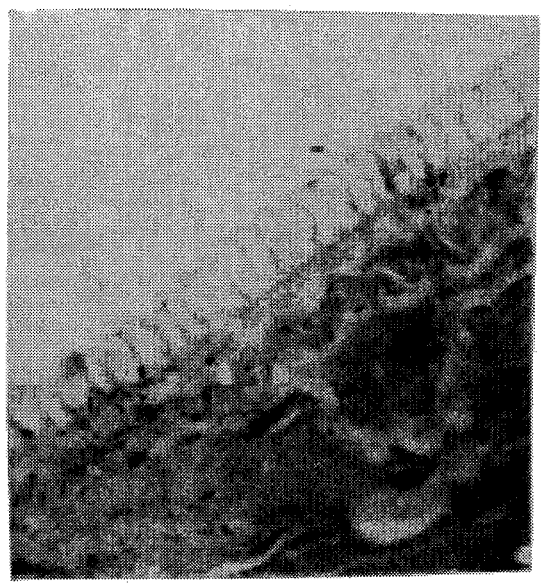
FIG. 3A–3C show the effects of cyclosporin A (CsA) on the ultrastructure of the cuticle of Brugia malayi L4 and adult stage parasites.

The present invention relates to the use of cyclophilin-like proteins (CLP) in a method for identifying compounds capable of binding to and/or inhibiting the enzymatic activity of these proteins. As noted above, CLP is a cyclophilin wherein the conserved tryptophan at the CsA drug binding domain has been substituted by another amino acid such as histidine. Compounds which bind CLP may be further screened for their ability to inhibit parasites which are not susceptible to the anti-parasitic effects of CsA as discussed in more detail below.

Generally, this method comprises contacting a CLP, e.g., the *B. malayi* CLP, with a compound to be tested (test compound) and measuring the binding and/or the change in enzymatic activity. The CLP may be affixed to a solid phase using, for example, an affinity chromatography system.

Using the method of the present invention, any compound may be tested. Preferably, the test compound is an CsA derivative. See, for example, Borel, *Transplantation Proc.*, 21:810–815 (1989). By the term CsA derivative it is meant a compound having one or more amino acid substitutions, or amino deletions, from the structure of CsA. As well as modified amino acids. A number of CsA derivative have been reported. See, e.g., *Merck Index*, pg. 431, 2759 (11th ed. 1989); Nelson, et al, *Journal of Immunology*, 150:2139–2147 (1993). Other CsA derivatives my be prepared using known synthetic methods. See, Nelson, et al, supra.

Most preferably, the CsA derivative is a binding site derivative. [Ke, et al., *Proc. Natl. Acad. Sci.*, USA, 88:9483–9487 (1991)]. Other compounds can be tested including, in particular, cyclic undecapeptides.

Compounds may also be designed that inhibit the PPiase activity of CLPs. The crystal structure of cyclophilin has recently been resolved as both as free form [Ke, et al., *Proc. Natl. Acad. Sci.*, USA, 88:9483– 9487 (1991)] and as a complex with CsA [Kallen, et al., *Nature*, 353:276–279 (1991); Kallen & Walkinshaw, FEBS Letters, 300:286-290 (1992); Pflugl, et al., *Nature*, 361:91–94 (1993)]. These studies were performed in order to design analogs of CsA with less toxic side effects in humans. Structure-based drug design can be employed in the same manner using three-dimensional structure information about histidine-containing cyclophilin. Computer analysis of the CLP structure and use of programs can be used to predict potential inhibitors that can then be tested using the method of the present invention.

Compounds showing promising activity can be further screened for in vitro and in vivo inhibition of parasitic nematode growth using, for example, the methods of Riberu, et al., *Am. J. Trop. Med. Hyg.*, 43:3–5 (1990) and Dedham *Animal Models in Parasitoloqy*, ed. D. Owen, p. 93, Mac-Millan, London (1982). Suitable screening methods are also set for in Example 2 hereof which follows.

In one embodiment, a fusion protein comprising the a CLP and protein having binding affinity for a substrate, e.g., malE, is used in an affinity chromatography system to screen and select binding compounds. Techniques for forming fusion proteins are well known to the skilled artisan. See, EPO 0 286 239 and J. Sambrook, et al., *Molecular Cloning: A Laboratory Manual*, Cold Spring Harbor Laboratory Press, Cold Spring Harbor, NY, p. 17.29–17.33 (1989)]. For convenience, commercially available systems may be used, including, for example, the Protein Fusion and Purification System from New England Biolabs; Beverly, Massachusetts. The fusion protein is then contacted with a substrate to which the binding protein has specific affinity such that the fusion protein is reversibly affixed to the column. A test compound is then added to the column. The compound may be labeled. The column is then washed and analyzed to determine the location of the compounds. Compounds found to have binding affinity for the fusion protein can then be tested for the ability to inhibit PPiase activity.

Binding proteins which may be employed in the method of the present invention include, for example, sugar binding proteins, such as maltose or arabinose binding protein, receptor binding proteins, amino acids binding proteins and metal binding proteins. Other binding proteins are well known to the skilled artisan. See, EPO 0 286 239 and N. M. Sassenfeld, *TIBTECH* 8:88–93 (1990).

In a preferred embodiment, a fusion protein comprising the *B. malayi* CLP (also referred to as Bmcyp-1) and maltose binding protein(MBP) is used in an affinity chromatography system to screen and select binding compounds. For example, using the *B. malayi* CLP/MBP fusion described in detail in Example 3 which follows, affinity columns can be prepared which will selectively bind to compounds, specific for the histidine-containing binding domain of *B. malayi*.

The fusion protein is loaded onto a 2.5×10 cm amylose column which has been previously equilibrated with 8 volumes of column buffer (20 mM TrisCl, 200 mM NaCl, 1 mM EDTA and 1 mM azide). The column can then be washed prior to the addition of the test compound. The test compounds are preferably added in equimolar ratios (in column buffer) to the fusion protein, and can be tagged with a radioactive marker, such as a tritium. The columns are then washed with column buffer and assayed both by scintillation counting and Bradford assay Bradford, *Analytical Biochem.*, 72:248 (1976)] to determine radioactivity and protein release, respectively in the flow-through fractions. When both radioactivity and protein levels have reached low or background levels, the column are then be eluted in 10 Mm maltose in column buffer and 3 ml fractions of the column eluate will be collected. Small samples (5 µl) of the eluted fractions can be analyzed both by scintillation and Bradford protein analysis, and together with samples from the column washing step are further analyzed by SDS PAGE analysis. The resultant SDS PAGE gels are stained by Coomassie to determine the protein profile of these samples and also analyzed by scintillation autoradiography (Amplify, Amersham), to determine the location of the radioactively-labelled compounds. In the event that labelled compounds are unavailable, similar analyses can be carried out by determining the location of protein in the various column fractions, and by analyzing these samples by SDS PAGE to determine molecular weight migration shifts due to the binding of the analog to the MBP-fusion protein.

This method can be used to determine which compounds, including cyclosporin A derivatives have the ability to bind to the cyclophilin-like protein of *B. malayi* and the other histidine-containing cyclophilins from other sources, including parasitic nematodes. Compound selected by this method can then be further analyzed for rotamase inhibitory activity using, for example, the method set forth below.

The peptidyl-prolyl cis-trans isomerase assay (PPiase) is a well characterized assay described by Fischer, et al, *Nature*, 337:476–478 (1989); Takahashi, et al., *Nature*, 337:473–475 (1989). The PPiase assay can be carried out as described in these references, with the modifications listed by Kofron, et al., *Biochemistry*, 30:6127–6134 (1991).

For example, 250mM of the substrate N-succinyl-Ala-Ala-Pro-Phe-$\rho$ -nitroaniline (Sigma) is dissolved in trifluoroethanol with 470 mM LiCl, and this is used at 5 nM per 1 ml reaction. 865 µl of the following buffer is used per reaction 50 mM HEPES & 100 mM NaCl pH8 at 0° C. (43 mM HEPES, 86 mM NaCl), and the chymotrypsin (Sigma) is used at 6 mg/ml from a 60 mg/ml stock (in 1 mM HCl). The recombinant Bmcyp-1 is used at 2–10 nM per reaction. Ten µl of the recombinant Bmcyp-1 is added to the above buffer and allowed to equilibrate on ice, then just before starting the assay 100 µl chymotrypsin is added. Finally 25

µl of the above substrate is added, the solution is mixed vigorously and readings are taken at 400 nm over 5 minutes.

To analyze the inhibitory effects of the various compounds, the above assay can be adapted by adding 10 µl of the test compound dissolved in DMSO (final concentrations ranging from 1–500nm) to the PPiase solution in the assay buffer. After preincubation for an appropriate period of time (10–150 min) at 10° C. the assay will be initiated by the addition of the chymotrypsin and the substrate. A direct comparison of the enzyme kinetics of Bmcpy-1 PPiase in the presence and absence of the test compound will reveal which compounds have histidine-binding PPiase inhibitory effects.

In another embodiment, the present invention relates a method of inhibiting the growth and development of parasites which are not susceptible to CsA. Generally, this method comprises contacting a parasite with, or administering to a host infected with said parasite, an effective amount of a compound which binds to and inhibits CLP activity in accordance with the above-described methodology.

According to the present invention, an "effective amount" of a compound is an amount sufficient to achieve the desired inhibition of parasite growth. It will be appreciated that the actually preferred amounts of compounds used will vary according to the specific compound being utilized, the particular compositions formulated and the mode of administration.

The compounds can be contacted with a parasite or administered to a host by any known means. For example, the compound may be directly administered to a parasite in culture. When the compound is administered to a host, any of a variety of means may be used, for example, parenteral injection (intramuscular (I.M.), intraperitoneal (I.P.), intravenous (I.V.), intracranial (I.C.) or subcutaneous (S.C.)), oral, inhaling through airways, or other known routes of administration.

The compounds can be administered in any means convenient, for example, it can be mixed with an inert carrier such as sucrose, lactose or starch. It can be in the form of tablets, capsules and pills. For parenteral administration, it will typically be injected in a sterile aqueous or non-aqueous solution, suspension or emulsion in association with a pharmaceutically-acceptable parenteral carrier such as physiological saline. Suitable pharmaceutical compositions can be formulated in accordance with known techniques such as those used in the formulation of CsA.

One CLP useful in the method of the present invention is the CLP from a parasitic nematode, the human filarial parasite *B. malayi*. This protein comprises 589 amino acids and has a predicted molecular weight of about 73 kDa. The DNA encoding the *B. malayi* CLP can be obtain from a 1823 bp cDNA inserted in pMal-c2 resulting in a plasmid designated BMCPY-1. A sample of an *E. coil* RR1 transformed with plasmid BMCPY-1 has been deposited with the American Type Culture Collection (ATCC) on Oct. 26, 1993 and received ATCC Accession No. 76693. The nucleotide sequence of the 1823 bp cDNA insert is set forth in the Sequence Listing as SEQ ID NO: 1. The *B. malayi* CLP amino acid sequence is set forth in the Sequence Listing as SEQ ID NO:2. Sequence analysis demonstrates that the *B. malayi* CLP has a histidine residue in place of the conserved tryptophan, established as being essential for binding to the drug CsA in other cyclophilins.

The DNA encoding the *B. malayi* CLP ( also referred to as Bmcpy 1) was isolated from an adult *B. malayi* cDNA library using as a probe an insert from a clone previously isolated from an adult *B. malayi* genomic expression library with an infective larval surface-specific monoclonal antibody [Awobuluyi, et al., *Mol. Biochem. Parasito.*, 44:149–152 (1991)] (see, Example 1).

The DNA encoding the *B. malayi* cyclophilin-like protein, or a fragment thereof, obtained from Bmcpy-1 can be used in the identification and isolation of related genes from other organisms, including other parasitic nematodes. For example, the DNA can be used in a Southern blot to screen for related genes from other organisms. Using the Bmcpy-1 cDNA as a Southern blot probe, the present inventors have determined the presence of related genes in the following parasites *Brugia pahangi*, *Dirofilaria immitis*, *Acanthocheilonema vitae*, *Litomosoides carinii*, and *Onchocerca gibsoni*.

A number a techniques familiar to the skilled artisan can be used to isolate DNA sequences corresponding to related CLP genes. For example, a cDNA or expression library is produced in a conventional manner by reverse transcription from messenger RNA (mRNA) from an organism found to possess related sequences, for example, by Southern blot analysis. To select clones containing DNA sequences encoding cyclophilin-like proteins, hybridization probes corresponding to portions of the Bmcyp-1 cDNA are produced and used to identify clones containing such sequences. Preferable probes include a fragment from nucleotide 326 to nucleotide 486 of SEQ ID NO:1. Screening of the expression library with antibodies generated against the *B. malayi* cyclophilin-like protein, or a fragment thereof, may also be used. Genomic libraries may also be used. Such techniques are taught, for example, in Sambrook, et al., *Molecular Cloning*, Second edition, CSH Laboratory Press (1989).

If desired, the DNA thus obtained can then be sub-cloned for further manipulation using techniques familiar to the skilled artisan. For example, the DNA can be subcloned into a vector such as pBR322 or pUC19.

Once identified, the DNA sequence coding for the CLP can be cloned into an appropriate expression vector such as a plasmid derived from *E. coil*, for example, pET3A, pBluescript or pUC19, the plasmids derived from the *Bacillus subtilis* such as pUB110, pTP5 and pC194, plasmids derived from yeast such as pSH19 and pSH15, bacteriophage such as , λ phage, bacteria such as *Agrobacterium tumefaciens*, animal viruses such as retroviruses and insect viruses such as Baculovirus.

Overexpression of the CLP can be achieved, for example, by separating the CLP from its endogenous control elements and then operably linking the polymerase gene to a very tightly controlled promoter such as a T7 expression vector. See, Rosenberg, et al, Gene, 56:125–135 (1987), which is hereby incorporated by reference. Insertion of the strong promoter may be accomplished by identifying convenient restriction targets near both ends of the CLP gene and compatible restriction targets on the vector near the promoter, and transferring the CLP gene into the vector in such an orientation as to be under transcriptional and translational control of the strong promoter.

CLP may also be overexpressed by utilizing a strong ribosome binding site placed upstream of the CLP gene to increase expression of the gene. See, Shine and Dalgarno, *Proc. Natl. Acad. Sci. USA*, 71:1342–1346 (1974).

The recombinant vector is introduced into the appropriate host using standard techniques for transformation and phage infection. For example, the calcium chloride method, as described by S.N. Cohen, *Proc. Natl. Acad. Sci. USA* 69:2110 (1972)is used for *E. coil*, the disclosure of which is incorporated by reference. The transformation of Bacillus is carried out according to the methods of S. Chang, et al., *Molecular and General Genetics*, 168:111 (1979), the disclosure of which is incorporated by reference. Transformation of yeast is carried out according to the method of Parent, et al., *Yeast*, 1:83–138 (1985), the disclosure of which is incorporated by reference. Certain plant cells can be transformed with *Agrobacterium tumefaciens*, according to the method described by C. H. Shaw, et al., *Gene*, 23:315 (1983), the disclosure of which is incorporated by reference. Transformation of animal cells is carried out according to, for example, the method described in *Virology*, 52:456 (1973), the disclosure of which is incorporated by reference. Transformation of insect cells with Baculovirus is carried out according to, for example, the method described in *Biotechnology*, 6:47 (1988), the disclosure of which is incorporated herein by reference.

The transformants are cultivated, depending on the host cell used, using standard techniques appropriate to such cells. For example, for cultivating *E. coli*, cells are grown in LB media at 30° C. to 42° C. to mid log or stationary phase.

The CLP can be isolated and purified from a culture of transformed host cells, for example, by either extraction from cultured cells or the culture solution.

When the CLP is to be extracted from a cultured cell, the cells are collected after cultivation by methods known in the art, for example, centrifugation. Then, the collected cells are suspended in an appropriate buffer solution and disrupted by ultrasonic treatment, lysozyme and/or freeze-thawing. A crude extract containing the CLP is obtained by centrifugation and/or filtration.

When the CLP is secreted into the culture solution, i.e., alone or as a fusion protein with a secreted protein such as maltose binding protein, the supernatant is separated from the cells by methods known in the art.

The separation and purification of CLP contained in the culture supernatant or the cell extract can be performed by the method described above, or by appropriate combinations of known separating and purifying methods. These methods include, for example, methods utilizing solubility such as salt precipitation and solvent precipitation, methods utilizing the difference in molecular weight such as dialysis, ultrafiltration, gel-filtration, and SDS-polyacrylamide gel electrophoresis, methods utilizing a difference in electric charge such as ion-exchange column chromatography, methods utilizing specific affinity chromatography, methods utilizing difference in hydrophobicity such as reverse-phase high performance liquid chromatography and methods utilizing a difference in isoelectric point such as isoelectric focusing electrophoresis.

The purified CLP can be used to produce antibodies, either polyclonal or monoclonal, useful in diagnostic assays.

The present invention also relates to methods for the identification of histidine-containing cyclophilins from other disease causing parasites of veterinary and medical importance. This method comprises using primers from the conserved cyclosporin A binding domain of cyclophilin, the amino acid sequence of the drug-binding domain can be determined in a variety of parasites responsible for important diseases. Those diseases caused by organisms which possess a histidine in place of tryptophan in the drug binding domain could potentially be treated with the compounds and analogs identified using the methods discussed above. This method has already identified two histidine-containing Cyclophilins from important disease-causing parasites, namely *D. immitis* (heartworm) and *O. gibsoni* (bovine onchocerciasis).

The present invention is further illustrated by the following Examples. These Examples are provided to aid in the understanding of the invention and are not construed as a limitation thereof.

The references cited above and below are herein incorporated by reference.

EXAMPLE 1

ISOLATION AND CHARACTERIZATION OF A DNA ENCODING THE *BRUGIA MALAYI* CYCLOPHILIN-LIKE PROTEIN

PREPARATION OF ADULT BRUGIA MALAYI cDNA LIBRARY

Messenger RNA from adult male *B. malayi* was purified by the guanidinium isothiocyanate method [Chomczynski & Sacchi, *Anal Biochem.*, 162:156–159 (1987)]. EcoR1 linkers (NEB 1019) were added and cDNA was packaged into the EcoR1 site of the expression vector λgt11 using the Stratagene Giga Pack Gold as per manufacturers instructions.

SCREENING THE *B. MALAYI* cDNA LIBRARY

An insert from genomic clone P2, previously isolated from an adult *B. malayi* genomic expression library using an infective larval surface-specific monoclonal antibody [Awobuluyi, *Mol. Biochem. Parasito.*, 44:149–152 (1991)] was labelled using a DNA random priming kit (New England BioLabs). The DNA was prepared from the λgt11 clone by thermal cycling, using the λgt11 forward and reverse primers (NEB 1288 & 1222). The template was then purified by phenol/chloroform, chloroform and ethanol extractions. Then cut with EcoR1 and finally separated on a 1% LMP-agarose gel, from which it was excised, digested overnight with 2U of β-agarose (NEB). The purified template (100 ng) was labelled for 2h at 37° C. with 50μCi of [$\alpha^{33}$P]dATP (NEN DuPont). The resulting probe was then purified away from free-counts on a Sephadex G-50 column (Pharmacia).

Nitrocellulose filters were prepared by Benton-Davis Plaque Lift Method [Benton & Davis, *Science*, 196:180–182 (1977)]. Duplicate filters containing a total of 50,000 plaques were hybridized with the labelled template overnight at 37° C., in hybridization solution (50% formamide, 2% SDS, 10% Denhardt's, and 5×SSC). The filters were subsequently washed extensively in 0.1%SDS, 0.1×SSC at 55 ° C. Approximately 150,000 plaques were screened using the randomly primed labelled probe. One positive plaque was present on the duplicating filters, and was taken through 4 rounds of plaque purification. This positive plaque was isolated and called Bmcyp-1.

CsCl ISOLATION OF λgt11 PHAGE DNA

DNA from the positive plaque was purified by CsCl gradient centrifugation. Briefly, ER1578 cells were infected with the Bmcyp-1 phage until lysis occurred, the supernatants were then extracted in chloroform then digested with DNase and RNase and precipitated overnight with 10%PEG. The pellet was then resuspended in SM buffer with 50 mM MgCl$_2$ and cholorform extracted. The resulting supernatant was then combined with 1.5 g/ml CsCl and centrifuged overnight at 35K. The purified Phage band was then dialyzed against SM and extracted with Proteinase K, 0.5M EDTA and SDS for 15min at 65° C. This was followed by one phenol extraction and four phenol/chloroform extractions, and the purified phage preparation was finally precipitated in ethanol and resuspended in 0.1M TE.

SUBCLONING INTO pUC19

Restrictions digests revealed that the Bmcyp-1 clone has one internal EcoR1 site, and therefore the two EcoR1 fragments were ligated independently into the EcoR1 site of the vector pUC19. In summary, pUC19 was cut with EcoR1, then treated with calf intestinal phosphate (NEB) for 1 h at 50° C. Ligations were then carried out at 1:1 vector to insert ratio, at 16° C. overnight with 1U T4 DNA ligase (NEB). The ligations were then transformed into RR1 competant cells (NEB), and resulting colonies were further selected by picking positive colonies and streaking onto a master and an 80 μg/ml X-GAL and 0. 1M IPTG plate for selection of white colonies. The presence of corresponding inserts was checked by performing thermal cycling with these clones using the pUC19 forward and reverse sequencing primers (1224 and 1233 NEB). Miniprep DNA was prepared from the positive plasmids using the Qiagen Kit according to the manufacturers' instructions.

SEQUENCING

The pUC19 subclones were completely sequenced in both forward and reverse directions using the NEB circumvent sequencing kit, according to manufacturers' recommendations. Primers used to obtain the sequence were the forward and reverse pUC19 primers (1244 and 1233 NEB), and primers synthesized independently corresponding to newly generated internal sequence.

NUCLEOTIDE AND DEDUCED AMINO ACID SEQUENCE OF Bmcyp-1

The nucleotide sequence of the Bmcyp-1 cDNA clone subcloned into pUC19 revealed an ORF from bp 57 throughout its entire 1823bp length. No stop condon has been observed (FIG. 1 (SEQ ID NO:1)). The resulting protein of 589 amino acids has a predicted molecular weight of 73,626 kDa.

When analyzed by the BLAST program the initial 176 amino acids of the amino-terminus were homologous to cyclophilin from a variety of species (FIG. 2 (SEQ ID NO:2)), with highest homologies to the cyclophilin-like proteins (CLPs) recently described from human and mouse [Anderson, *Proc. Natl. Acad. Sci. USA*, 90:542–546 (1993)], cyclophilin-40 proteins of bovine and human origin [Kieffer, et al., *J. Biol. Chem.*, 268:12303–12310 (1993)] and plant cyclophilins including *Arabidopsis thaliana* [Bartling, *Plant Mol. Biol*, 19:529–530(1992)]. In common with the CLPs, cyp-40s and plant cyclophilins, Bmcyp-1 has an 8 amino acid insert (residues 51-58; FIG. 2 (SEQ ID NO:2)) not found in the more common cyclophilins such as human cyclophilin A. This insert contains at least 2 amino acids (GK) shared between all these species, and in the case of Human cyp-40, bovine cyp-40 and tomato cyclophilin this identity is over a 5 amino acid stretch (GKPLH). The remaining 413 amino acid carboxyl-terminal region of Bmcyp-1 was likewise analyzed, and it also revealed significant homology to the mouse and human CPLs [Anderson, et al., *Proc. Natl. Acad. Sci. USA*, 90:542–546 (1993)], and, in common with the CLPs the carboxyl-terminus of Bmcyp-1 is highly hydrophilic and contains many serine and arginine residues. Bmcyp-1, therefore possesses two major domains, an N-terminal cyclophilin region and a hydrophilic C-terminal domain.

Bmcyp-1 does not posses the conserved sole tryptophan residue (position 121) of cyp-18 (Human cyp A) which has been established as being essential for binding to the drug CsA [Lui, et al., *Biochemistry*, 30:2306–2310 (1991)]. As with the most closely related cyclophilins mentioned above, *Brugia* cyclophilin contains a histidine in its place (position 131) (FIG. 2 (SEQ ID NO:2): indicated). The absence of this CsA binding dependant residue led to the hypothesis that the *Brugia* protein would have a reduced or absent affinity for this drug, an observation which has recently been found for the mouse and human CLPs both of which do not bind to a CsA column and require a CsA concentration of 800 nM to inhibit rotamase activity, compared to 20 nM for human cyclophilin C (Stephen Anderson personal communication). Likewise the other closely related cyclophilins, cyp-40 from human and bovine, require 300 nM of CsA to inhibit rotamase activity [Kieffer, et al., *J. Biol. Chem.*, 268:12303–12310 (1993)].

EXAMPLE 2

EFFECT OF CsA ON SUSCEPTIBLE (*CAENORHABDITIS ELEGANS*) AND RESISTANT (*B. MALAYI*) AND NEMATODE SPECIES

Cyclophilin genes have also recently been isolated from the free-living nematode *Caenorhabditis elegans*, and like the more common cyclophilins these also posses the conserved tryptophan in their CsA binding domain [McCombie, et al., *Nature Genet.*, 1:124–131 (1992)]. Experiments were therefore designed to investigate the association between the presence or absence of the tryptophan residue and susceptibility of nematodes to CsA. These experiments were carried out with Brugia malayi (histidine) and *Caenorhabditis elegans* (tryptophan). CsA was administered (50 mg/Kg) to gerbils on days 2, 9, 20 and 46 post infection with *B. malayi* L3s. L4s and adults were collected and numbers were found not to differ between control and CsA-treated gerbils. The C. elegans were grown for 13 days on agar plates supplemented with CsA diluted from 1 μg to 1 mg/ml in agar. In this experiment the high CsA concentration had a clear detrimental effect on the numbers of viable nematodes, killing those cultured at 1 mg/ml.

CsA caused a clear decrease of nematode numbers and severely effected the motility of those remaining at concentrations of 500 μg/ml and 100 μg/ml. A large proportion of the nematodes present on plates at these concentrations were clearly damaged, appearing folded and limp.

Figure 3B:
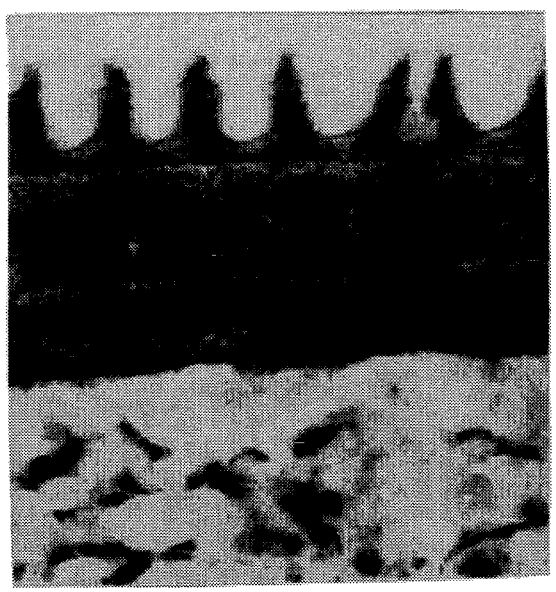
Figure 3C:
Figure 4A:
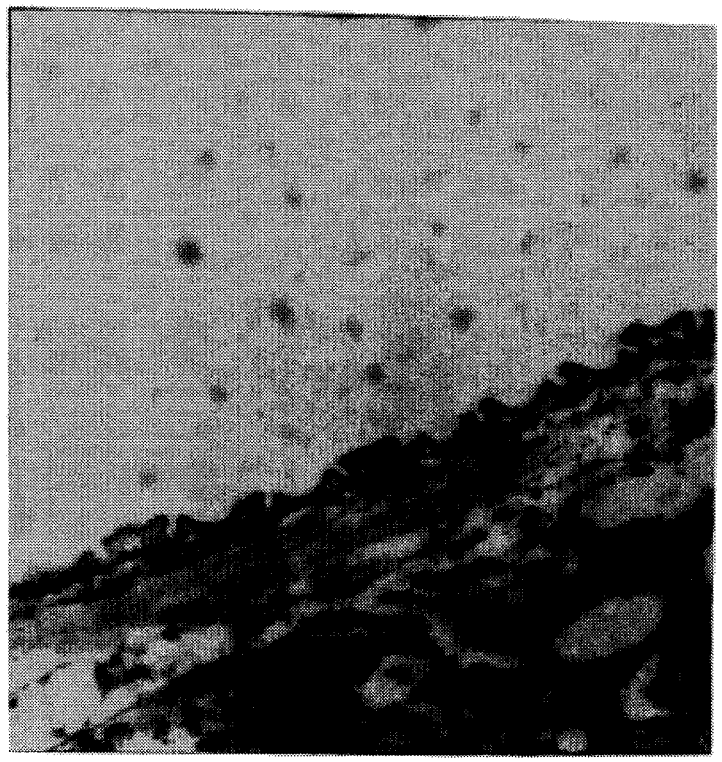
FIG. 4A–4D shows the effects of cyclosporin A (CsA) on the ultrastructure of the cuticle of Caenorhabditis elegans.
Figure 4B:
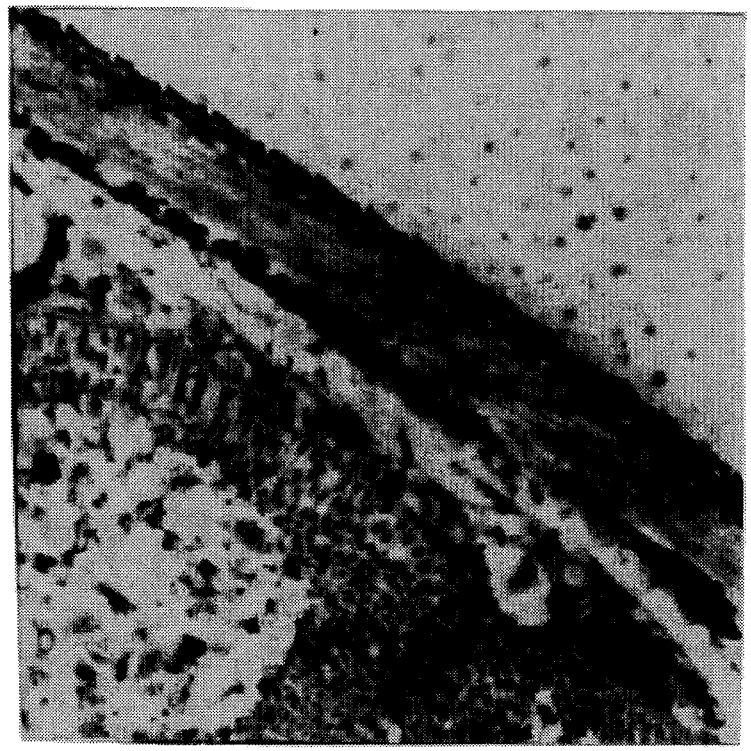
Figure 4C:
Figure 4D:

Both *B. malayi* and *C. elegans* CsA-treated nematodes and their corresponding controls were processed for ultrastructural analysis at the EM level to determine the site of action of the drug, with particular respect to their tegumental surfaces. FIG. 3 & 4 summarize some of the results obtained in this study. At the ultrastructural level there were no cuticular differences noted between *B. malayi* parasites removed from a CsA treated host or a control treated host, either at the L4 or adult stages (FIG. 3: A, B & C). When *C. elegans* was examined however, a dramatic effect of increasing concentrations of CsA was noted on the structural integrity of the cuticle. In nematodes grown on control plates and plates where CsA was at a low concentration (1– 20 μg/ml) no effect was noted (FIG. 4: A & B). Nematodes grown at 100 μg/ml and especially 500 μg/ml had severe lesions in their cuticles (FIG. 4: C & D). High concentrations of CsA in the agar plates caused detachment of the cuticle at the hypodermal layer, perhaps indicating that an old cuticle was shed, with a failure to synthesis a new cuticle in the rapid manner which is characteristic of nematode moults.

EXAMPLE 3

PURIFICATION AND CHARACTERIZATION OF RECOMBINANT Bmcyp-1

SUBCLONING INTO pMALc AND EXPRESSION OF MBF FUSION PROTEINS

Thermal cycling was carried out with specifically designed primers to allow directional cloning into the pMAL-c2 vector (New England BioLabs). The 5' primer corresponded to the ORF of Bmcyp-1, and had an upstream BamHl restriction site incorporated (forward 5'-GGG-GATCC ATGTCAAAAAAAGATCGGCG (SEQ ID NO: 16)). The other primer corresponding to the 3' end of this clone had a downstream stop codon and HindIII restriction site engineered into it (reverse 5'-CGGAAGCTTCA GAAT-TCCGGCTCTCTTTCTCT (SEQ ID NO: 17)). The Bmcyp-1 λgt11 CsCl template (250 ng) and the primers (80 ng) were used in a reaction with vent $^{exo-}$(New England BioLabs). Ten reactions, each of 18 cycles of 94° C. for 30 sec, 54° C. for 30 sec and 72° C. for 2 min were carried out and the resulting products were pooled phenol/chloroform extracted, chloroform extracted and precipitated in ethanol on the presence of 1M NaCl. The subsequent pellet was then resuspended in 0.1M TE and cut to completion with HindIII and BamHl. The cut product was then run on a 1% low melt-point agarose gel, excised and digested overnight with 2U of β-Agarose (New England BioLabs). The resultant supernatant was then ethanol precipitated and resuspended in 0.1 M TE.

LIGATION INTO pMAL-c2

Ligations and transformations were essentially carried out as described in the New England BioLabs Protein Fusion and Purification System Instruction manual. Briefly, the pMAL-c2 vector was cut with BamHl and HindIII and ligations of 1:1 vector to insert ratios were employed. Ligations were allowed to proceed 2h at 16° C. with 1U T4 DNA ligase (New England BioLabs). The ligation mix was incubated at 65° C. for 5 min and 25 µl of competent cells (ER2252) were added, mixed on ice for 5 min, heated to 42° C. for 2 min, mixed with 100 µl of LB at 37° C. for 20 min and then plated out on LBamp plates and allowed to grow overnight.

Positive transformants were further selected by picking positive colonies and streaking onto a master and a plate with 80 µg/ml X-GAL and 0.1M IPTG for selection of white colonies. Miniprep DNA was prepared from the positive clones using the Qiagen miniprep system, following the manufacturers' recommendations.

PRODUCTION AND PURIFICATION OF MBP Bmcyp-1

A single MBP-Bmcyp-1 colony was picked and grown overnight at 37° C in 10 ml of LB amp, this was then transferred to 1L of prewarmed rich broth plus amp. The cells were grown at 37° C. to log phase then induced for 2h with 0.3 mM IPTG. Following centrifugation at 5,000×g, the pelleted cells were resuspended in 50 ml of column buffer (20 mM TrisCl, 200 mM NaCl, 1 mM EDTA and 1 mM azide) and frozen overnight at −20° C. The following day the suspension was thawed in cold water, sonicated for 3 main with 15 sec pulses, The sonicate was the centrifuged at 9,0000×g and the supernatant was loaded onto a 2.5×10 cm amylose column which had been equilibrated with 8 volumes of column buffer. The column was then subsequently washed with 10 column volumes of buffer and finally eluted with column buffer plus 10 mM maltose. This procedure yielded 5 mg of fusion protein/L which consisted of four major bands on a SDS-PAGE gel, migrating at approximately 68, 80, 100 and 115 kDa, the most dominant product was the 68 kDa protein.

FACTOR XA CUTTING

The optimal time and concentration of factor Xa to allow cutting of the fusion was determined to be overnight at room temperature with 1% factor Xa. This allowed complete excision of the MBP-fusion, resulting in products which migrated at approximately 28, 24, and 14 kDa, the sum of which would correspond to the expected full length product, therefore indicating the presence of factor Xa susceptible sites within the recombinant protein. The factor Xa cut recombinant protein was then purified away from the MBP by applying the mixture to a Mono-S (S-sepharose) column in 50 mM sodium phosphate buffer (pH 7), resulting in concentration of the MBP in the flow through, and elution of the cleaved recombinant proteins as a single peak in 200 mM NaCl (FIG. 5).

RESULTS

As set forth in detail above, to allow directional subcloning into the pMAL-c2 vector a set of specific primers were generated. The 5' primer corresponded to the ORF of Bmcyp-1, and had an upstream BamHl restriction site incorporated. The other primer corresponding to the 3' end of this clone had a downstream stop codon and HindIII restriction site engineered into it. Thermal Cycle sequencing was performed using the above primers and the λgt11 CsCl purified Bmcyp-1 DNA as template. The resulting product was then purified and ligated into the pMAL-c2 vector, and the fusion protein was expressed in ER2252 competent cells, which after induction was analyzed by SDS PAGE.

Figure 5:
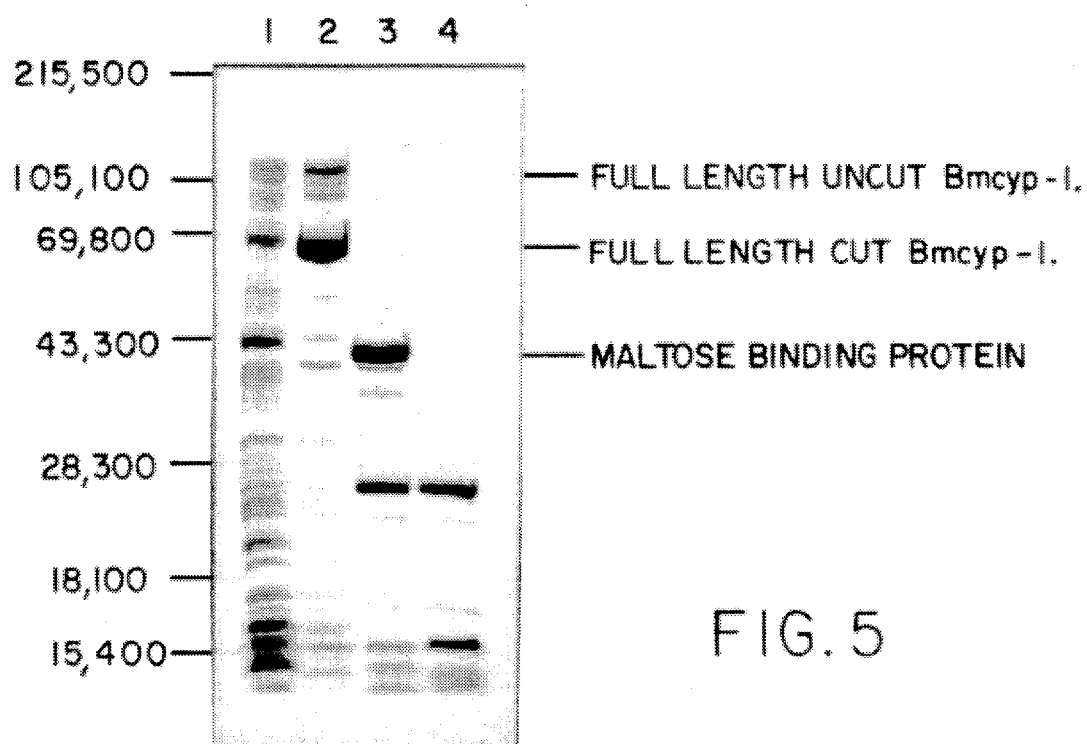
FIG. 5 shows the expression of Bmcyp-1 in the maltose binding fusion protein system. Lane I is Mbp-Bmcyp-1 cell sonicate. Lane 2 is Mbp-Bmcyp-1 eluted from amylose column. Lane 3 is Mbp-Bmcyp-1 eluate cut with 1% factor Xa. Lane 4 is Mbp-Bmcyp-1 purified on mono-S column.

FIG. 5 depicts the fusion protein, its subsequent amylose column purification, factor X cutting and further purification on a mono-S column. Lane 1 reveals the complex profile of the sonicated cell supernatant before amylose purification. Lane 2 depicts the profile of proteins eluted with 10 mM maltose from an amylose column, this procedure selectively purifies the fused proteins, revealing four major high molecular weight components of approximately 115 kDa, 100 kDa, 80 kDa and 68 kDa. This indicates that there is breakdown of the full-length fusion protein with the 115 kDa protein being the uncut full-length fusion (arrow), and the 68 kDa its most dominant breakdown product. The proteins in lane 3 are of the same preparation as lane 2, except that they were cleaved overnight with 1% factor 10, this procedure reveals the presence of cleaved MBP (upper band at 43 kDa, arrow), a major 25 kDa product corresponding to the 68 kDa fusion minus the MBP, there are also some minor products of 37 kDa and 14 kDa. Finally lane 4 reveals the protein of the material from lane 3 eluted in 200 mM NaCl from a Mono-S column, indicating complete separation of the major cleaved breakdown product of 25 kDa from the MBP, as well a small quantities of the full-length 73 kDa protein (arrow), and the breakdown products of 37 and 14 kda.

ROTAMASE ASSAY

The rotamase or peptidyl-protyl cis-trans isomerase (PPiase) assay was essentially carried out as described by Fischer, et al., *Nature*, 337:476–478 (1989), using the substrate solvent modifications described by Kofron, et al., *Biochem.*, 30:6127–6134 (1991). This assay determines the rate of cis to trans conversion of a proline containing tetrapeptide, which is susceptible to chymotrypsin proteolysis only when in the trans configuration, and whose cleavage results in the release of a chromogenic dye. Briefly, to a 1 ml cuvette 1 nM (10 µl) of MBP-Bmcyp-1 enzyme was added to 850 µl PPiase buffer (50 mM HEPES; 86 mM NaCl ; pH 8 at 0° C.) and allowed to equilibrate on ice. Just before starting the assay 100 µl (6 mg/ml) chymotrypsin was added followed by 25 µl of a 1 nM Ala-Ala-Pro-Phe-P-nitroanalide (dissolved in Trifluroethanol with 470 mM LiCl). The cuvette was inverted rapidly and placed in the spectrophotometer and readings were taken at regular intervals over a 5 min period at OD $_{400}$. All reactions in this assay were carried out at 4° C.

ROTAMASE ACTIVITY OF Bmcyp-1

Initial results indicate that MBP-Bmcyp-1 fusion protein, like all the other cyclophilins described to date has PPiase activity. This activity is however lower than that of native human cyclophilin A, when compared at identical molar concentrations. The existence of a lower PPiase activity is expected since the fusion is much larger (115 kDa compared to 18 kDa), and it is being expressed in *E. coli* and not a native form.

WESTERN BLOT OF NATIVE AND RECOMBINANT ANTIGENS WITH ANTI-Bmcyp-1 ANTISERA

Figure 6:
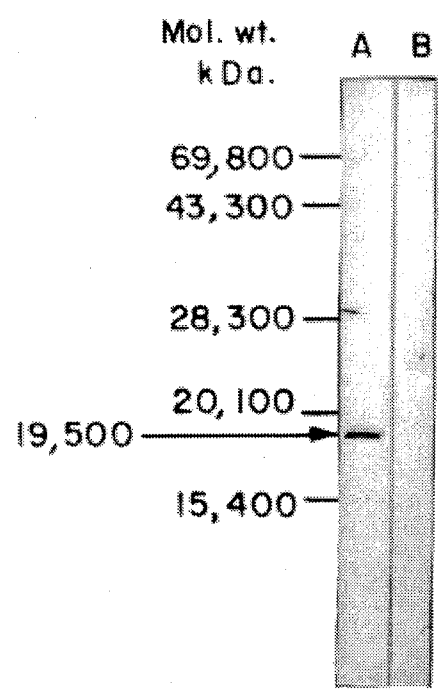
FIG. 6 shows the Western blot analysis of adult Brugia malayi extract with antisera to unfused Bmcyp-1. Lane A is anti-Bmcyp-1 (Fx cut) and lane B is normal mouse sera.

Western blot analysis using sera raised against both uncut and cut fusion protein identified a specific band migrating at approximately 19.5 K in adult *Brugia malayi* PBS extracts (FIG. 6). This result may imply that the *Brugia cyclophilin* is post-transnationally processed to remove the hydrophilic tail leaving only the cyclophilin domain intact.

EXAMPLE 4

ANALYSIS OF Bmycp-1 EXPRESSION IN DIFFERENT HELMINTH SPECIES

Figure 8:
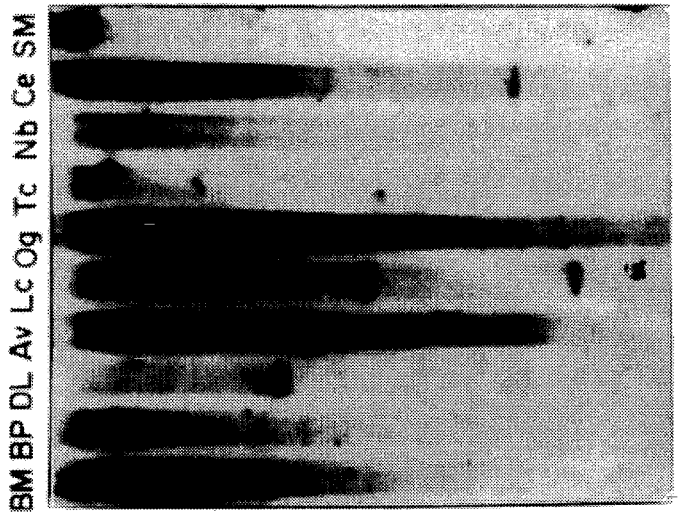
FIG. 8 is a Southern blot of Helminth DNA using the cyclophilin domain of Bmcyp-1 cDNA as a probe. BM - Brugia malayi; BP - Brugia pahangi; AV- A. vitae; LC - L. carinii; TC - Toxocara canis; Nb - Nippostrongylus brasiliensis; CE - Caenorhabditis elegans; and SM - Schistosoma mansoni.
Figure 7:
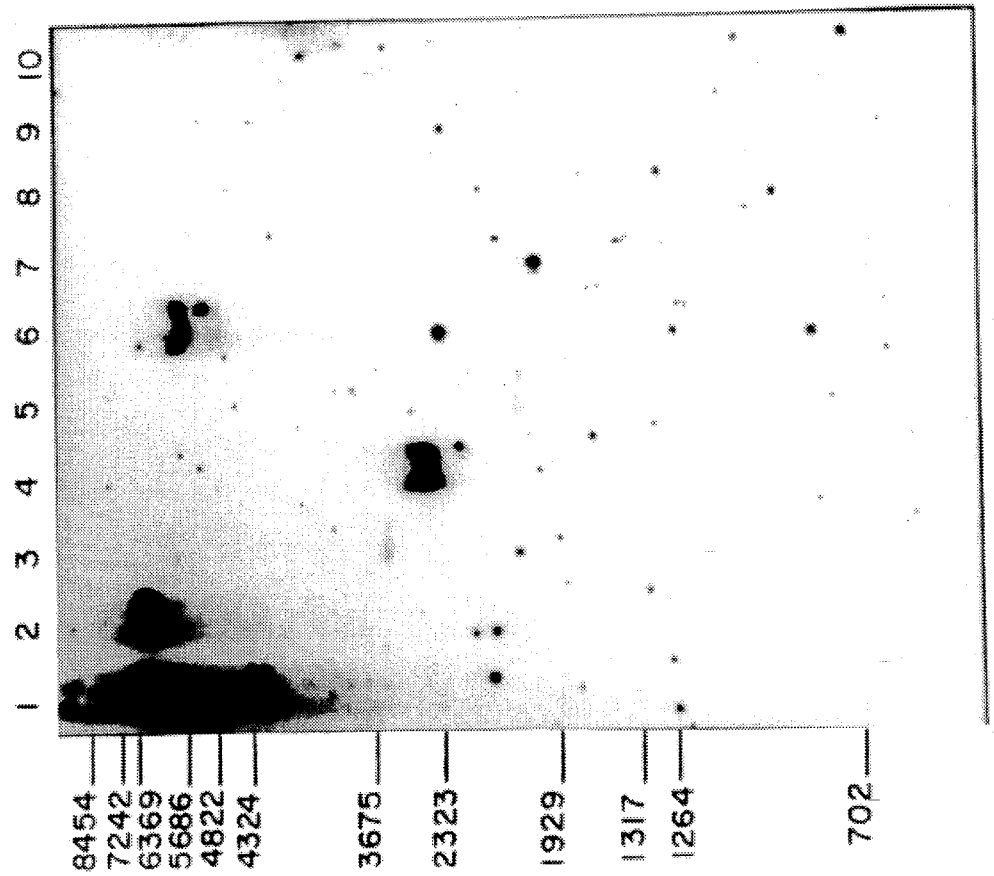
FIG. 7 shows the Southern blot of Helminth DNA probed with Bmcyp-1. Lane 1 is Brugia malayi; lane 2 is Brugia pahangi; lane 3 is Dirofilaria immitis; lane 4 is Acanthocheilonema vitae; lane 5 is Litomosoides carinii; lane 6 is Onchocerca gibsoni; lane 7 is Toxocara canis; lane 8 is Nippostrongylus brasiliensis; lane 9 is Caenorhabditis elegans and lane 10 is Schistosoma mansoni.

Southern blotting was carried out to determine the presence of similar cyclophilin genes in other nematode and trematode species. Southern blotting using the entire Bmcyp-1 cDNA as a probe revealed that similar genes were also present in the filarial nematodes *B. pahangi*, *D. immitis*, *Acanthocheilonema viteae*, *Litomosoides carinii* and *Onchocerca gibsoni*, but not in the non-filarial nematodes *Toxocara canis*, *Nippostrongylus brasilienis*, *C. elegans* and the parasitic trematode *Schistosoma mansoni* (FIG. 7). This result was consistent whether the stringency was high (37° C. hybridization/55° C. wash) or (25° C. hybridization/25° C. wash). At low stringency, more fragments were noted for the filarial species *D. immitis*, *A. viteae, and L. carinii*, the sum of which were approximately equivelent to the size of the *B. malayi* genes, indicating that HindIII sites may be within these genes. The above Southerns were therefore repeated using only the cyclophilin domain of Bmcyp-1 cDNA as a probe, and this analysis revealed identical results for the above species when applied at high stringency, as only the filarial species had a corresponding gene. However, when the same probe was applied at a low stringency all nematode and the single trematode species were revealed as having a corresponding cyclophilin gene (FIG. 8).

SOUTHERN BLOT CONDITIONS

HYBRIDIZATION

Hybridization solution: 10% hybridization tris-EDTA, 25% 20X SSC, 50% formamide, 2% SDS and 10% Denhardts solution.

HYBRIDIZATION CONDITIONS

High stringency - Hybridization overnight at 37° C.

Low stringency - Hybridization overnight at room temperature 20° C.

WASHING CONDITIONS

High stringency - 0. 1% SSC and 0. 1% SDS at 55 ° C.

Low stringency - 0.1% SSC and 0.1% SDS at room temperature 20° C.

EXAMPLE 5

THERMAL CYCLING AMPLIFICATION OF CONSERVED CYCLOPHILIN DOMAIN FROM DIFFERENT NEMATODES

Using primers corresponding to the highly conserved domain of the Bmcyp-1 sequence, PCR was performed on genomic DNA from different nematode species. These DNA fragments were then further purified and sequenced to identify if these species contain the histidine residue in place of the conserved tryptophan in the CsA-binding domain.

POLYMERASE CHAIN REACTION

Genomic DNA analyzed was from the filarial nematodes *Brugia malayi*, *Achanthechielonema vitae*, *Dirofilaria immitis*, *Litomosoides carinii*, *Onchocerca gibsoni* and the strongylid nematode *Nippostrongylus brasiliesis*.

1 µg of genomic DNA was mixed with 200 ng of primers C2.7–C 10 (forward 5'-GGTGGTATGTTTGACGATGAGC (SEQ ID NO:18)) and (Cyp-8 Reverse 5'-CAACCTTAC-CAAATACCACATG (SEQ ID NO: 19)). Dntps and BSA were added, and the volume made up to 98 µl with sterile distilled water. Finally 3 µl of vent exo(-) polymerase (NEB) was added and the reaction mixture was overlayed with oil. Reactions were cycled 25 times at 92° C. for 1 min., 53° C. for 1 min., and 72° C. for 1 min.

PCR products were then purified by phenol/chloroform extraction, and ethanol precipitation, resuspended in tris-EDTA and then used as templates for sequencing.

Sequencing was performed using the NEB circumvent sequencing kit, following the protocol for kinase labelled primers.

RESULTS

This analysis revealed that the nematodes had DNA sequences very similar to the Bmcyp-1, this was especially true for filarial nematodes where the changes which were present were usually silent third base changes. All the filarial species possessed a histidine in place of tryptophan, as was revealed for Bmcyp-1.

It should be understood that the examples and embodiments described herein are for illustrative purposes only and that various modifications or changes in light thereof will be suggested to persons skilled and purview of this Application and the scope of the appended claims.

What is claimed is:

1. A substantially pure protein endogenous to *Brugia malayi* having a molecular weight of about 73 kDa, wherein said protein possesses peptidyl-propyl cis-trans isomerase activity and contains a histidine rather than a tryptophan amino acid in the Cyclosporin A binding domain.

2. The protein of claim 1, wherein the amino acid sequence of the proteins include the amino acids of SEQ ID NO:21.

* * * * *

UNITED STATES PATENT AND TRADEMARK OFFICE
CERTIFICATE OF CORRECTION

PATENT NO. : 5,482,850
DATED : January 9, 1996
INVENTOR(S) : Carlow, et. al.

It is certified that error appears in the above-indentified patent and that said Letters Patent is hereby corrected as shown below:

Column 7, line 53    replace "BMCPY-1" with --BMCYP-1

Column 7, line 54    replace "BMCPY-1" with --BMCYP-1--

Column 7, line 56    replace "76693" with --75593--

Column 7, line 66    replace "Bmcpy 1" with --Bmcyp-1--

Signed and Sealed this

Ninth Day of April, 1996

*Attest:*

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,482,850

DATED : January 9, 1996

INVENTOR(S) : Carlow, et al.

It is certified that error appears in the above-indentified patent and that said Letters Patent is hereby corrected as shown below:

Column 1, line 21, replace "posses" with --possess--

Column 1, line 39, replace "It also" with --It has also--

Column 1, line 48, after "FKBP" insert --,--

Column 1, line 48, replace "its" with --their--

Column 1, line 53, delete "to"

Column 2, line 5, replace "vitae" with --viteae--

Column 2, line 29, replace "vitae" with --viteae--

Column 2, line 34, replace "between" with --with--

Column 3, line 35, replace "vitae" with --viteae--

Column 4, lines 11-12, replace "are blocked and the residues having identity with Brugia malayi are highlighted." with --are indicated.--

Column 4, line 16, replace "Csa" with --CsA--

Column 4, line 27, replace "Csa" with --CsA--

Column 4, line 29, replace "Csa" with --CsA--

Column 4, line 31, replace "Csa" with --CsA--

Column 4, line 35, replace "Mbp" with --MBP--

Column 4, line 36, replace "Mbp" with --MBP--

UNITED STATES PATENT AND TRADEMARK OFFICE
CERTIFICATE OF CORRECTION

PATENT NO. : 5,482,850
DATED : January 9, 1996
INVENTOR(S) : Carlow, et al.

It is certified that error appears in the above-indentified patent and that said Letters Patent is hereby corrected as shown below:

Column 4, line 37, replace "Mbp" with --MBP--

Column 4, line 38, replace "Mbp" with --MBP--

Column 4, line 45, replace "*vitae*" with --*viteae*--

Column 4, line 52, replace "*vitae*" with --*viteae*--

Column 5, line 14, replace "derivative" with --derivatives--

Column 5, line 17, replace "my" with --may--

Column 5, line 26, replace "as free form" with --free form--

Column 5, line 42, replace "Dedham" with --Denham--

Column 5, line 46-47, replace "a CLP and" with --CLP and a--

Column 6, line 27, replace "the column are" with --bound material can--

Column 6, line 44, replace "derivatives have" with --derivatives, have--

Colummn 7, line 24, replace "actually" with --actual--

Column 7, line 51, replace "obtain" with --obtained--

Column 8, line 6, replace "Bmcpy-1" with --Bmcyp-1--

Column 8, line 14, replace "*vitae*" with --*viteae*--

Column 8, line 48, replace "polymerase" with --CLP--

UNITED STATES PATENT AND TRADEMARK OFFICE
CERTIFICATE OF CORRECTION

PATENT NO. : 5,482,850

DATED : January 9, 1996

INVENTOR(S) : Carlow, et al.

It is certified that error appears in the above-indentified patent and that said Letters Patent is hereby corrected as shown below:

Column 10, line 36, replace "ß-agarose" with --ß-agarase--

Column 10, line 62, replace "cholorform" with --chloroform--

Column 10, line 64, replace "Phage" with --phage--

Column 11, line 5, replace "Restrictions" with --Restriction--

Column 11, line 10, replace "phosphate" with --alkaline phosphate--

Column 11, line 15, replace "a master" with --a master,--

Column 11, line 16, replace "IPTG plate" with --IPTG, plating containing--

Column 11, line 57, replace "Human" with --human--

Column 12, line 8, replace "dependant" with --dependent--

Column 12, line 14, replace "cyclophilin C" with --cyclophilin A--

Column 12, line 29, replace "posses" with --possess--

Column 12, line 45, replace "of" with --in--

Column 12, line 57, delete "treated" (Both occurrences)

Column 13, line 10, replace "MBF" with --MBP--

Column 13, line 31, replace "ß-Agarose" with --ß-Agarase--

Column 13, line 50, replace "master and" with --master plate, and--

UNITED STATES PATENT AND TRADEMARK OFFICE
CERTIFICATE OF CORRECTION

PATENT NO. : 5,482,850

DATED : January 9, 1996

INVENTOR(S) : Carlow, et al.

It is certified that error appears in the above-indentified patent and that said Letters Patent is hereby corrected as shown below:

Column 14, line 16, replace "excision" with --removal--

Column 14, line 16, delete "fusion"

Column 14, line 21, delete "away"

Column 14, line 47, replace "fused" with --fusion--

Column 14, line 66, replace "protyl" with --propyl--

Column 15, line 37, replace "transnationally" with --translationally--

Column 15, line 52, replace "*brasilienis*" with --*brasiliensis*--

Column 15, line 55, replace "wash) or (25" with --wash) or low (25--

Column 16, line 35, replace "*Achanthechielonema vitae*" with --*Achantheochielonema viteae*--

Signed and Sealed this

Twenty-third Day of July, 1996

BRUCE LEHMAN

Attest:

Attesting Officer

Commissioner of Patents and Trademarks

UNITED STATES PATENT AND TRADEMARK OFFICE
CERTIFICATE OF CORRECTION

PATENT NO. : 5,482,850
DATED : January 9, 1996
INVENTOR(S) : Carlow, et al.

It is certified that error appears in the above-indentified patent and that said Letters Patent is hereby corrected as shown below:

Column 1, line 35, replace "*E. coil*" with --*E. coli*--

Column 1, line 60, replace "Plasmodium species" with --*Plasmodium species*--

Column 2, line 15, replace "in vitro" with --*in vitro*--

Column 5, line 40, replace "in vitro and in vivo" with --*in vitro* and *in vivo*--

Column 6, line 23, replace "Bradford, *Analytical*" with --[Bradford, *Analytical*--

Column 6, line 57, replace "N-succinyI" with --N-succinyl--

Column 6, line 63, replace "mg/mi" with --mg/ml--

Column 7, line 53, replace "*coil*" with --*coli*--

UNITED STATES PATENT AND TRADEMARK OFFICE
CERTIFICATE OF CORRECTION

PATENT NO. : 5,482,850
DATED : January 9, 1996
INVENTOR(S) : Carlow, et al.

It is certified that error appears in the above-indentified patent and that said Letters Patent is hereby corrected as shown below:

Column 8, line 50, replace "Gene" with --*Gene*--

Column 8, line 67, replace "(1972) is used for *E. coil*" with --(1972) is used for *E. coli*--

Column 10, line 28-29, replace ( 1991 ) ]" with --(1991)]--

Column 10, line 31, replace "theλgt11" with --the λgt11--

Column 13, line 67, replace "main" with --min--

Signed and Sealed this

Third Day of December, 1996

Attest:

BRUCE LEHMAN

Attesting Officer     Commissioner of Patents and Trademarks